(12) United States Patent
Wilson et al.

(10) Patent No.: US 7,163,956 B2
(45) Date of Patent: Jan. 16, 2007

(54) SUBSTITUTED FULLERENE COMPOSITIONS AND THEIR USE AS ANTIOXIDANTS

(75) Inventors: Stephen R. Wilson, Ringgold, VA (US); Yi-Zhen Hu, Eugene, OR (US); Tong Zhu, Houston, TX (US); Russ Lebovitz, Houston, TX (US)

(73) Assignee: C Sixty Inc., Houston, TX (US)

( * ) Notice: Subject to any disclaimer, the term of this patent is extended or adjusted under 35 U.S.C. 154(b) by 294 days.

(21) Appl. No.: 10/960,449

(22) Filed: Oct. 7, 2004

(65) Prior Publication Data

US 2005/0130939 A1 Jun. 16, 2005

Related U.S. Application Data

(60) Provisional application No. 60/606,779, filed on Sep. 2, 2004, provisional application No. 60/510,455, filed on Oct. 10, 2003, provisional application No. 60/510,598, filed on Oct. 10, 2003, provisional application No. 60/510,283, filed on Oct. 10, 2003.

(51) Int. Cl.
*A61K 31/40* (2006.01)
*A61K 31/95* (2006.01)
*C07C 63/00* (2006.01)
*C07C 211/00* (2006.01)
*C07D 487/00* (2006.01)

(52) U.S. Cl. ............ 514/410; 514/561; 514/569; 514/532; 514/646; 548/417; 560/8; 562/405; 564/305

(58) Field of Classification Search ........ 514/410, 514/561, 569, 532, 646; 548/417; 560/8; 562/405; 564/305
See application file for complete search history.

(56) References Cited

U.S. PATENT DOCUMENTS

| | | | | |
|---|---|---|---|---|
| 5,648,523 A | 7/1997 | Chiang | | 562/100 |
| 5,739,376 A | 4/1998 | Bingel | | 560/51 |
| 5,811,460 A | 9/1998 | Friedman et al. | | 514/563 |
| 5,972,993 A | 10/1999 | Ptchelintsev | | 514/449 |
| 5,994,410 A | 11/1999 | Chiang et al. | | 514/709 |
| 6,162,926 A | 12/2000 | Murphy et al. | | 548/417 |
| 6,204,391 B1 | 3/2001 | Friedman et al. | | 548/338.1 |
| 6,265,443 B1 | 7/2001 | Choi et al. | | 514/569 |
| 6,380,434 B1 * | 4/2002 | Chiang | | 564/458 |
| 6,399,785 B1 | 6/2002 | Murphy et al. | | 548/417 |
| 6,448,412 B1 | 9/2002 | Murphy et al. | | 548/417 |
| 6,452,037 B1 | 9/2002 | Chiang | | 560/102 |
| 6,506,928 B1 | 1/2003 | Hirsch | | 560/80 |
| 6,538,153 B1 | 3/2003 | Hirsch et al. | | 560/82 |
| 6,765,098 B1 * | 7/2004 | Nakamura et al. | | 548/338.1 |
| 6,777,445 B1 * | 8/2004 | Lei et al. | | 514/557 |
| 6,790,963 B1 * | 9/2004 | Chiang et al. | | 548/417 |
| 6,890,676 B1 * | 5/2005 | Nuber et al. | | 429/33 |
| 6,949,660 B1 * | 9/2005 | Chiang et al. | | 548/517 |
| 7,008,713 B1 * | 3/2006 | Nuber et al. | | 429/33 |
| 7,018,599 B1 * | 3/2006 | Nakamura et al. | | 423/414 |
| 7,071,406 B1 * | 7/2006 | Smalley et al. | | 136/252 |
| 2002/0098180 A1 | 7/2002 | Lei et al. | | 424/125 |
| 2003/0027870 A1 | 2/2003 | Wilson et al. | | 514/656 |
| 2003/0162837 A1 | 8/2003 | Dugan et al. | | 514/574 |
| 2003/0180491 A1 | 9/2003 | Hirsch et al. | | 428/35.7 |

FOREIGN PATENT DOCUMENTS

WO WO99/43358 9/1999
WO WO00/44357 8/2000

OTHER PUBLICATIONS

Dugan et al., *Parkinsonism and Related Disorders* 7:243-246 (2001).
Dugan et al., *Neurobiology of Disease* 3:129-135 (1996).
Dugan et al., *Proc. Natl. Acad. Sci. USA* 94:9434-9439 (Aug. 1997).
Gharbi et al., *ECS Proceedings* (May 14-19, 2000).
Wilson, "Biological Aspects of Fullerenes," Chapter 10, *Fullerenes: Chemistry, Physics and Technology*, K. Kadish and R. Ruoff eds., 2000 John Wiley & Sons NY, NY.
Chiang et al., *J. Chem. Soc., Chem. Commun.*, pp. 1283-1284 (1995).
Fumelli et al., *The Journal of Investigative Dermatology* 115:835-841 (Nov. 2000).
Straface et al., *FEBS Letters* 454:335-340 (1999).
Lotharius e al., *The Journal of Neuroscience* 19(4):1284-1293 (Feb. 15, 1999).
Lin et al., *Journal of Neurochemistry* 72(4):1634-1640 (1999).
Lin et al., *Neuroscience Research* 43:317-321 (2002).
Monti et al., *Biomedical and Biophysical Research Communications* 277:711-717 (2000).
Tsao et al., *Journal of Antimicrobial Chemotherapy* 49:641-649 (2002).
Huang et al., *Eur. J. Biochem.* 254:38-43 (1998).

\* cited by examiner

*Primary Examiner*—Deborah C. Lambkin
(74) *Attorney, Agent, or Firm*—Williams, Morgan & Amerson, P.C.

(57) ABSTRACT

This patent discloses a substituted fullerenes, compositions comprising the same, and their use as antioxidants. The substituted fullerenes comprise a fullerene core (Cn) and at least one of: (i) from 1 to 6 ($>CX^1X^2$) groups bonded to the fullerene core; (ii) from 1 to 18 —$X^3$ groups bonded to the fullerene core; (iii) from 1 to 6 —$X^4$— groups bonded to the fullerene core; or (iv) from 1 to 6 dendrons bonded to the fullerene core.

38 Claims, 17 Drawing Sheets

C3 is Chiral - two mirror images

50a →

← 50b

52a →

← 52b

| Compound | Ref. No. | IC$_{50}$ (µM) |
|---|---|---|
| Trolox (Comparative) | 110 | 440 |
|  C3 (Comparative) | 111 | 174 |
|  R = -CH$_2$CH$_2$CH$_2$COOH Long-chain C3 | 1201 | 42 |

| | | |
|---|---|---|
| <br>D3: R = H<br>(Comparative) | 112 | 965 |
| <br>long-chain D3: R = CH$_2$CH$_2$CH$_2$COOH | 1205 | 264 |
| <br>Trans-2 | 1206 | 90 |

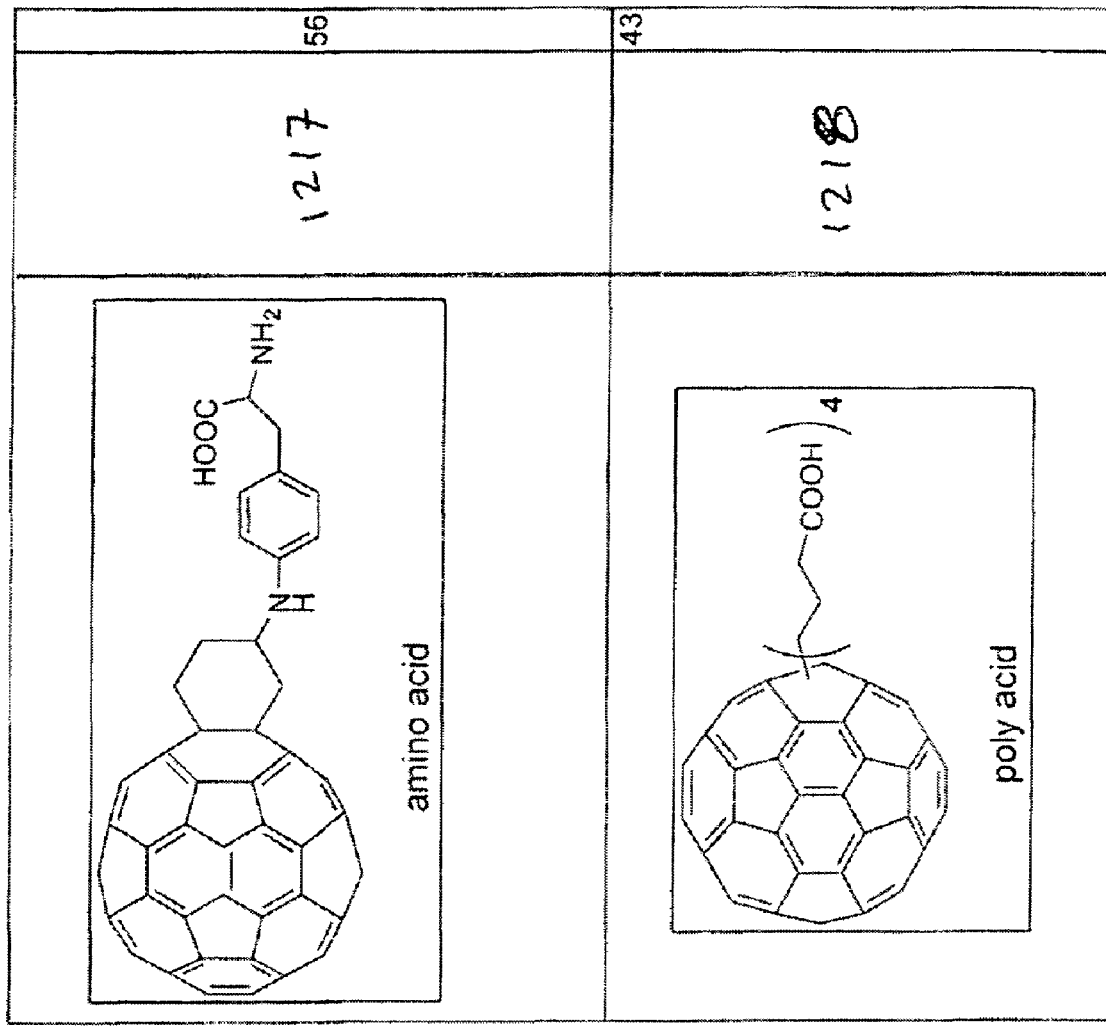

SUBSTITUTED FULLERENE COMPOSITIONS AND THEIR USE AS ANTIOXIDANTS

This application claims priority from prior copending U.S. provisional patent applications Ser. Nos. 60/510,455; 60/510,598; and 60/510,283, all filed on Oct. 10, 2003, and Ser. No. 60/606,779, filed Sep. 2, 2004.

BACKGROUND OF THE INVENTION

The present invention relates generally to the field of substituted fullerenes. More particularly, it concerns substituted fullerenes and their use in compositions to ameliorate oxidative stress diseases or provide other antioxidant activities.

Reactive oxygen species (ROS), commonly referred to as "free radicals," have been implicated in a variety of diseases. ROS are believed to promote, in at least certain cells, cell types, tissues, or tissue types, cell death (apoptosis), impaired cellular function, and modification or change in proportion of extracellular matrix components such as elastin or collagen, among other symptoms.

Buckminsterfullerenes, also known as fullerenes or, more colloquially, "buckyballs," are cage-like molecules consisting essentially of $sp^2$-hybridized carbons. Fullerenes were first reported by Kroto et al., Nature (1985) 318:162. Fullerenes are the third form of pure carbon, in addition to diamond and graphite. Typically, fullerenes are arranged in hexagons, pentagons, or both. Most known fullerenes have 12 pentagons and varying numbers of hexagons depending on the size of the molecule. Common fullerenes include $C_{60}$ and $C_{70}$, although fullerenes comprising up to about 400 carbon atoms are also known.

$C_{60}$ has 30 carbon-carbon double bonds, and has been reported to readily react with oxygen radicals (Krusic et al., Science (1991) 254:1183–1185). Other fullerenes have comparable numbers of carbon-carbon double bonds and would be expected to be about as reactive with oxygen radicals. However, native fullerenes are generally only soluble in apolar organic solvents, such as toluene or benzene. To render fullerenes water-soluble, as well as to impart other properties to fullerene-based molecules, a number of fullerene substituents have been developed.

Methods of substituting fullerenes with various substituents are known in the art. Methods include 1,3-dipolar additions (Sijbesma et al., J. Am. Chem. Soc. (1993) 115: 6510–6512; Suzuki, J. Am. Chem. Soc. (1992) 114:7301–7302; Suzuki et al., Science (1991) 254:1186–1188; Prato et al., J. Org. Chem. (1993) 58:5578–5580; Vasella et al., Angew. Chem. Int. Ed. Engl. (1992) 31:1388–1390; Prato et al., J. Am. Chem. Soc. (1993) 115:1148–1150; Maggini et al., Tetrahedron Lett. (1994) 35:2985–2988; Maggini et al., J. Am. Chem. Soc. (1993) 115:9798–9799; and Meier et al., J. Am. Chem. Soc. (1994) 116:7044–7048), Diels-Alder reactions (Iyoda et al., J. Chem. Soc. Chem. Commun. (1994) 1929–1930; Belik et al., Angew. Chem. Int. Ed. Engl. (1993) 32:78–80; Bidell et al., J. Chem. Soc. Chem. Commun. (1994) 1641–1642; and Meidine et al., J. Chem. Soc. Chem. Commun. (1993) 1342–1344), other cycloaddition processes (Saunders et al., Tetrahedron Lett. (1994) 35:3869–3872; Tadeshita et al., J. Chem. Soc. Perkin. Trans. (1994) 1433–1437; Beer et al., Angew. Chem. Int. Ed. Engl. (1994) 33:1087–1088; Kusukawa et al., Organometallics (1994) 13:4186–4188; Averdung et al., Chem. Ber. (1994) 127:787–789; Akasaka et al., J. Am. Chem. Soc. (1994) 116:2627–2628; Wu et al., Tetrahedron Lett. (1994) 35:919–922; and Wilson, J. Org. Chem. (1993) 58:6548–6549); cyclopropanation by addition/elimination (Hirsch et al., Agnew. Chem. Int. Ed. Engl. (1994) 33:437–438 and Bestmann et al., C. Tetra. Lett. (1994) 35:9017–9020); and addition of carbanions/alkyl lithiums/Grignard reagents (Nagashima et al., J. Org. Chem. (1994) 59:1246–1248; Fagan et al., J. Am. Chem. Soc. (1994) 114:9697–9699; Hirsch et al., Agnew. Chem. Int. Ed. Engl. (1992) 31:766–768; and Komatsu et al., J. Org. Chem. (1994) 59:6101–6102); among others. The synthesis of substituted fullerenes is reviewed by Murphy et al., U.S. Pat. No. 6,162,926.

Bingel, U.S. Pat. No. 5,739,376, and related published applications, is believed to be the first to report tris-malonate fullerene compounds, referred to below as C3 and D3. Dugan and coworkers at Washington University, St. Louis, have reported that C3 and D3 are useful for neuroprotection against amyotrophic lateral sclerosis (ALS, colloquially Lou Gehrig's disease) and related neurodegenerative diseases which are caused by oxidative stress injury (Choi et al., U.S. Pat. No. 6,265,443; Dugan et al., Parkinsonism Rel. Disorders 7:243–246 (2001); Dugan et al., Proc. Nat. Acad Sci. USA, 93:9434–9439 (1997); and Lotharius et al., J. Neurosci. 19:1284–1293 (1999)). C3 and (to a lesser extent) D3 have also been shown to provide either in vitro or in vivo benefits in protecting against other oxidative stress injuries (Fumelli et al., J. Invest. Dermatol. 115:835–841 (2000); Straface et al., FEBS Lett. 454:335–340 (1999); Monti et al., Biochem. Biophys. Res. Commun. 277:711–717 (2000) Lin et al., Neurosci. Res. 43:317–321 (2002); Huang et al., Eur. J. Biochem. 254:38–43 (1998); and Leonhardt, PCT Publ. Appln. WO 00/44357) and in inhibiting Gram-positive bacteria (Tsao et al., J. Antimicrob. Chemother. 49:641–649 (2002)).

Although C3 and D3 are capable of at least some scavenging of reactive oxygen species implicated in oxidative stress diseases, a need remains for fullerene derivatives which can ameliorate oxidative stress diseases, and especially for such fullerene derivatives which are superior to C3 or D3.

SUMMARY OF THE INVENTION

In one embodiment, the present invention relates to a substituted fullerene, comprising a fullerene core (Cn), wherein n is an even integer greater than or equal to 60, and at least one of i-iv:

(i) m ($>CX^1X^2$) groups bonded to the fullerene core, wherein:

(i-a) m is an integer from 1 to 6, inclusive, (i-b) each $X^1$ and $X^2$ is independently selected from —H; —COOH; —CONH$_2$; —CONHR'; —CONR'$_2$; —COOR'; —CHO; —(CH$_2$)$_d$OH; a peptidyl moiety; —R; —RCOOH; —RCONH$_2$; —RCONHR'; —RCONR'$_2$; —RCOOR'; —RCHO; —R(CH$_2$)$_d$OH; a heterocyclic moiety; a branched moiety comprising one or more terminal —OH, —NH$_2$, triazole, tetrazole, or sugar groups; or a salt thereof, wherein each R is a hydrocarbon moiety having from 1 to about 6 carbon atoms and each R' is independently a hydrocarbon moiety having from 1 to about 6 carbon atoms, an aryl-containing moiety having from 6 to about 18 carbon atoms, a hydrocarbon moiety having from 1 to about 6 carbon atoms and a terminal carboxylic acid or alcohol, or an aryl-containing moiety having from 6 to about 18 carbon atoms and a terminal carboxylic acid or alcohol, and d is an integer from 0 to about 20; and (i-c) when m is 3, at least one $X^1$ or $X^2$ is not —COOH;

(ii) p —$X^3$ groups bonded to the fullerene core, wherein:

(ii-a) p is an integer from 1 to 18, inclusive; and (ii-b) each —$X^3$ is independently selected from —$N^+(R^2)(R^3)(R^4)$, wherein $R^2$, $R^3$, and $R^4$ are independently —H or —$(CH_2)_d$—$CH_3$, wherein d is an integer from 0 to about 20; —$N^+(R^2)(R^3)(R^8)$, wherein $R^2$ and $R^3$ are independently —H or —$(CH_2)_d$—$CH_3$, wherein d is an integer from 0 to about 20, and each $R^8$ is independently —$(CH_2)_f$—$SO_3^-$, —$(CH_2)_f$—$PO_4^-$, or —$(CH_2)_f$—$COO^-$, wherein f is an integer from 1 to about 20; —$C(R^5)(R^6)(R^7)$, wherein $R^5$, $R^6$, and $R^7$ are independently —COOH, —H, —CH(=O), —$CH_2OH$, or a peptidyl moiety; —$C(R^2)(R^3)(R^8)$, wherein $R^2$ and $R^3$ are independently —H or —$(CH_2)_d$—$CH_3$, wherein d is an integer from 0 to about 20, and each $R^8$ is independently —$(CH_2)_f$—$SO_3^-$, —$(CH_2)_f$—$PO_4^-$, or —$(CH_2)_f$—$COO^-$, wherein f is an integer from 1 to about 20; —$(CH_2)_e$—COOH, —$(CH_2)_e$—$CONH_2$, —$(CH_2)_e$—COOR', wherein e is an integer from 1 to about 6 and each R' is independently a hydrocarbon moiety having from 1 to about 6 carbon atoms, an aryl-containing moiety having from 6 to about 18 carbon atoms, a hydrocarbon moiety having from 1 to about 6 carbon atoms and a terminal carboxylic acid or alcohol, or an aryl-containing moiety having from 6 to about 18 carbon atoms and a terminal carboxylic acid or alcohol; a peptidyl moiety; or an aromatic heterocyclic moiety containing a cationic nitrogen;

(iii) q —$X^4$— groups bonded to the fullerene core, wherein (iii-a) q is an integer from 1 to 6, inclusive; and (iii-b) each —$X^4$— group is independently

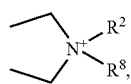

wherein $R^2$ is independently —H or —$(CH_2)_d$—$CH_3$, d is an integer from 0 to about 20, and $R^8$ is independently —$(CH_2)_f$—$SO_3^-$, —$(CH_2)_f$—$PO_4^-$, or —$(CH_2)_f$—$COO^-$, and f is an integer from 1 to about 20;

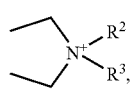

wherein each $R^2$ and $R^3$ is independently —H or —$(CH_2)_d$—$CH_3$ and d is an integer from 0 to about 20; or

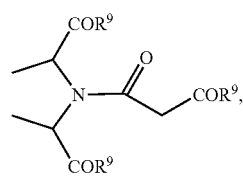

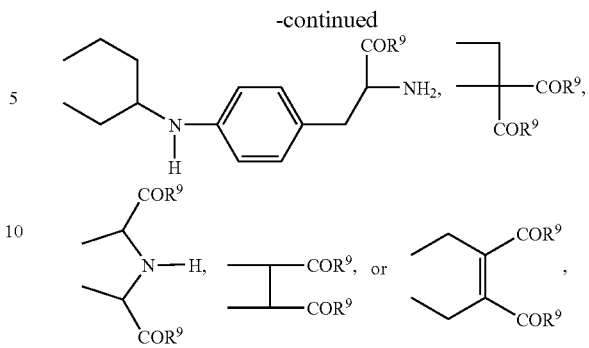

wherein each $R^2$ is independently —H or —$(CH_2)_d$—$CH_3$, d is an integer from 0 to about 20, and each $R^9$ is independently —H, —OH, —OR', —$NH_2$, —NHR', —$NHR'_2$, or —$(CH_2)_d OH$, wherein each R' is independently a hydrocarbon moiety having from 1 to about 6 carbon atoms, an aryl-containing moiety having from 6 to about 18 carbon atoms, a hydrocarbon moiety having from 1 to about 6 carbon atoms and a terminal carboxylic acid or alcohol, or an aryl-containing moiety having from 6 to about 18 carbon atoms and a terminal carboxylic acid or alcohol.

(iv) r dendrons bonded to the fullerene core and s nondendrons bonded to the fullerene core, wherein:

(iv-a) r is an integer from 1 to 6, inclusive;

(iv-b) s is an integer from 0 to 18, inclusive;

(iv-b) each dendron has at least one protic group which imparts water solubility, (iv-d) each nondendron independently comprises at least one drug, amino acid, peptide, nucleotide, vitamin, or organic moiety, and (iv-e) when r is 1 and the dendron comprises 18 —COOH groups, s is an integer from 1 to 18, inclusive.

Herein, the word "or" has the inclusive meaning wherever it appears.

In another embodiment, the present invention relates to a composition comprising the substituted fullerene referred to above and a carrier.

In yet another embodiment, the present invention relates to a method of ameliorating an oxidative stress disease, comprising administering to a mammal an effective amount of a composition comprising a carrier and a substituted fullerene, wherein the substituted fullerene is as described above.

In still another embodiment, the present invention relates to a method of ameliorating damage to tissues for transplantation, ameliorating spoilage of food, inhibiting microbes, or reducing free radical levels in tobacco, comprising contacting the tissues for transplantation, the food, the microbes, or the tobacco with an effective amount of a composition comprising a substituted fullerene and a carrier, wherein the substituted fullerene is as described above.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 10A–10H report the IC50 values for various substituted fullerenes (and Trolox, a known non-fullerene antioxidant), as described in Example 1.

DESCRIPTION OF ILLUSTRATIVE EMBODIMENTS

Figure 1A:
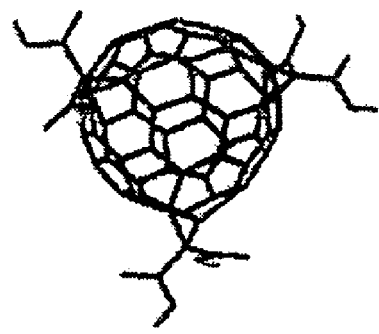
FIG. 1A shows an exemplary substituted fullerene in structural formula.
Figure 1B:
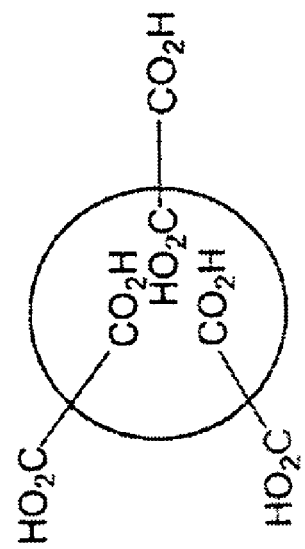
FIG. 1B shows the same substituted fullerene in a schematic formula.

In one embodiment, the present invention relates to a substituted fullerene, comprising a fullerene core (Cn), wherein n is an even integer greater than or equal to 60, and at least one of i-iv:

(i) m ($>CX^1X^2$) groups bonded to the fullerene core, wherein:
  (i-a) m is an integer from 1 to 6, inclusive,
  (i-b) each $X^1$ and $X^2$ is independently selected from —H; —COOH; —CONH$_2$; —CONHR'; —CONR'$_2$; —COOR'; —CHO; —(CH$_2$)$_d$OH; a peptidyl moiety; —R; —RCOOH; —RCONH$_2$; —RCONHR'; —RCONR'$_2$; —RCOOR'; —RCHO; —R(CH$_2$)$_d$OH; a heterocyclic moiety; a branched moiety comprising one or more terminal —OH, —NH$_2$, triazole, tetrazole, or sugar groups; or a salt thereof, wherein each R is a hydrocarbon moiety having from 1 to about 6 carbon atoms and each R' is independently a hydrocarbon moiety having from 1 to about 6 carbon atoms, an aryl-containing moiety having from 6 to about 18 carbon atoms, a hydrocarbon moiety having from 1 to about 6 carbon atoms and a terminal carboxylic acid or alcohol, or an aryl-containing moiety having from 6 to about 18 carbon atoms and a terminal carboxylic acid or alcohol, and d is an integer from 0 to about 20; and
  (i-c) when m is 3, at least one $X^1$ or $X^2$ is not —COOH;
(ii) p —$X^3$ groups bonded to the fullerene core, wherein:
  (ii-a) p is an integer from 1 to 18, inclusive; and
  (ii-b) each —$X^3$ is independently selected from —N$^+$(R$^2$)(R$^3$)(R$^4$), wherein R$^2$, R$^3$, and R$^4$ are independently —H or —(CH$_2$)$_d$—CH$_3$, wherein d is an integer from 0 to about 20; —N$^+$(R$^2$)(R$^3$)(R$^8$), wherein R$^2$ and R$^3$ are independently —H or —(CH$_2$)$_d$—CH$_3$, wherein d is an integer from 0 to about 20, and each R$^8$ is independently —(CH$_2$)$_f$—SO$_3^-$, —(CH$_2$)$_f$—PO$_4^-$, or —(CH$_2$)$_f$—COO$^-$, wherein f is an integer from 1 to about 20; —C(R$^5$)(R$^6$)(R$^7$), wherein R$^5$, R$^6$, and R$^7$ are independently —COOH, —H, —CH(=O), —CH$_2$OH, or a peptidyl moiety; —C(R$^2$)(R$^3$)(R$^8$), wherein R$^2$ and R$^3$ are independently —H or —(CH$_2$)$_d$—CH$_3$, wherein d is an integer from 0 to about 20, and each R$^8$ is independently —(CH$_2$)$_f$—SO$_3^-$, —(CH$_2$)$_f$—PO$_4^-$, or —(CH$_2$)$_f$—COO$^-$, wherein f is an integer from 1 to about 20; —(CH$_2$)$_e$—COOH, —(CH$_2$)$_e$—CONH$_2$, —(CH$_2$)$_e$—COOR', wherein e is an integer from 1 to about 6 and each R' is independently a hydrocarbon moiety having from 1 to about 6 carbon atoms, an aryl-containing moiety having from 6 to about 18 carbon atoms, a hydrocarbon moiety having from 1 to about 6 carbon atoms and a terminal carboxylic acid or alcohol, or an aryl-containing moiety having from 6 to about 18 carbon atoms and a terminal carboxylic acid or alcohol; a peptidyl moiety; or an aromatic heterocyclic moiety containing a cationic nitrogen;

(iii) q —$X^4$— groups bonded to the fullerene core, wherein
  (iii-a) q is an integer from 1 to 6, inclusive; and
  (iii-b) each —$X^4$— group is independently

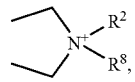

wherein R$^2$ is independently —H or —(CH$_2$)$_d$—CH$_3$, d is an integer from 0 to about 20, and R$^8$ is independently —(CH$_2$)$_f$—SO$_3^-$, —(CH$_2$)$_f$—PO$_4^-$, or —(CH$_2$)$_f$—COO$^-$, and f is an integer from 1 to about 20;

wherein each R$^2$ and R$^3$ is independently —H or —(CH$_2$)$_d$—CH$_3$ and d is an integer from 0 to about 20; or

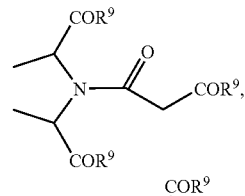

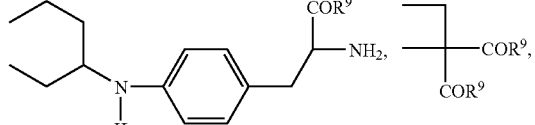

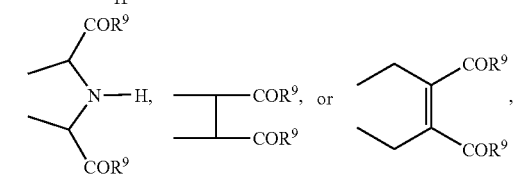

wherein each R$^2$ is independently —H or —(CH$_2$)$_d$—CH$_3$, d is an integer from 0 to about 20, and each R$^9$ is independently —H, —OH, —OR', —NH$_2$, —NHR', —NHR'$_2$, or —(CH$_2$)$_d$OH, wherein each R' is independently a hydrocarbon moiety having from 1 to about 6 carbon atoms, an aryl-containing moiety having from 6 to about 18 carbon atoms, a hydrocarbon moiety having from 1 to about 6 carbon atoms and a terminal carboxylic acid or alcohol, or an aryl-containing moiety having from 6 to about 18 carbon atoms and a terminal carboxylic acid or alcohol.

(iv) r dendrons bonded to the fullerene core and s nondendrons bonded to the fullerene core, wherein:
(iv-a) r is an integer from 1 to 6, inclusive;
(iv-b) s is an integer from 0 to 18, inclusive;
(iv-b) each dendron has at least one protic group which imparts water solubility,
(iv-d) each nondendron independently comprises at least one drug, amino acid, peptide, nucleotide, vitamin, or organic moiety, and
(iv-e) when r is 1 and the dendron comprises 18 —COOH groups, s is an integer from 1 to 18, inclusive.

All ranges given herein include the endpoints of the ranges, unless explicitly stated to the contrary.

Buckminsterfullerenes, also known as fullerenes or, more colloquially, buckyballs, are cage-like molecules consisting essentially of $sp^2$-hybridized carbons and have the general formula ($C_{20+2m}$) (where m is a natural number). Fullerenes are the third form of pure carbon, in addition to diamond and graphite. Typically, fullerenes are arranged in hexagons, pentagons, or both. Most known fullerenes have 12 pentagons and varying numbers of hexagons depending on the size of the molecule. "$C_n$" refers to a fullerene moiety comprising n carbon atoms.

Common fullerenes include $C_{60}$ and $C_{70}$, although fullerenes comprising up to about 400 carbon atoms are also known.

Fullerenes can be produced by any known technique, including, but not limited to, high temperature vaporization of graphite. Fullerenes are available from MER Corporation (Tucson, Ariz.) and Frontier Carbon Corporation, among other sources.

A substituted fullerene is a fullerene having at least one substituent group bonded to at least one carbon of the fullerene core. Exemplary substituted fullerenes include carboxyfullerenes and hydroxylated fullerenes, among others.

A carboxyfullerene, as used herein, is a fullerene derivative comprising a $C_n$ core and one or more substituent groups, wherein at least one substituent group comprises a carboxylic acid moiety or an ester moiety. Generally, carboxyfullerenes are water soluble, although whether a specific carboxyfullerene is water soluble is a matter of routine experimentation for the skilled artisan.

In another embodiment, the fullerene can be a hydroxylated fullerene. A "hydroxylated fullerene," as used herein, is a fullerene derivative comprising a $C_n$ core and one or more substituent groups, wherein at least one substituent group comprises a hydroxyl moiety.

In all embodiments, the substituted fullerene comprises a fullerene core (Cn), which can have any number of carbon atoms n, wherein n is an even integer greater than or equal to 60. In one embodiment, the Cn has 60 carbon atoms (and may be represented herein as $C_{60}$). In one embodiment, the Cn has 70 carbon atoms (and may be represented herein as $C_{70}$).

Throughout this description, particular embodiments described herein may be described in terms of a particular acid, amide, ester, or salt conformation, but the skilled artisan will understand an embodiment can change among these and other conformations depending on the pH and other conditions of manufacture, storage, and use. All such conformations are within the scope of the appended claims. The conformational change between, e.g., an acid and a salt is a routine change, whereas a structural change, such as the decarboxylation of an acid moiety to —H, is not a routine change.

In one embodiment, the substituted fullerene comprises a fullerene core (Cn) and m ($>CX^1X^2$) groups bonded to the fullerene core. The notation ">C" indicates the group is bonded to the fullerene core by two single bonds between the carbon atom "C" and the Cn. The value of m can be an integer from 1 to 6, inclusive.

$X^1$ can be selected from —H; —COOH; —CONH$_2$; —CONHR'; —CONR'$_2$; —COOR'; —CHO; —(CH$_2$)$_d$OH; a peptidyl moiety; a heterocyclic moiety; a branched moiety comprising one or more terminal —OH, —NH$_2$, triazole, tetrazole, or sugar groups; or a salt thereof, wherein each R' is independently (i) a hydrocarbon moiety having from 1 to about 6 carbon atoms, (ii) an aryl-containing moiety having from 6 to about 18 carbon atoms, (iii) a hydrocarbon moiety having from 1 to about 6 carbon atoms and a terminal carboxylic acid or alcohol, or (iv) an aryl-containing moiety having from 6 to about 18 carbon atoms and a terminal carboxylic acid or alcohol, and d is an integer from 0 to about 20. In one embodiment, $X^1$ can be selected from —R, —RCOOH, —RCONH$_2$, —RCONHR', —RCONR'$_2$, —RCOOR', —RCHO, —R(CH$_2$)$_d$OH, a peptidyl moiety, or a salt thereof, wherein R is a hydrocarbon moiety having from 1 to about 6 carbon atoms. In one embodiment, $X^1$ can be selected from —H; —COOH; —CONH$_2$; —CONHR'; —CONR'$_2$; —COOR'; —CHO; —(CH$_2$)$_d$OH; a peptidyl moiety; —R; —RCOOH; —RCONH$_2$; —RCONHR'; —RCONR'$_2$; —RCOOR'; —RCHO; —R(CH$_2$)$_d$OH; a heterocyclic moiety; a branched moiety comprising one or more terminal —OH, —NH$_2$, triazole, tetrazole, or sugar groups; or a salt thereof.

A heterocyclic moiety is a moiety comprising a ring, wherein the atoms forming the ring are of two or more elements. Common heterocyclic moieties include those comprising carbon and nitrogen, among others.

A branched moiety is a moiety comprising at least one carbon atom which is bonded to three or four other carbon atoms, wherein the moiety does not comprise a ring. In one embodiment, the branched moiety comprising one or more terminal —OH, —NH$_2$, triazole, tetrazole, or sugar groups can be selected from —R(CH$_2$)$_d$C(COH)$_g$(CH$_3$)$_{g-3}$, —R(CH$_2$)$_d$C(CNH$_2$)$_g$(CH$_3$)$_{g-3}$, —R(CH$_2$)$_d$C(C[tetrazol])$_g$(CH$_3$)$_{g-3}$, —R(CH$_2$)$_d$C(C[triazol])$_g$(CH$_3$)$_{g-3}$, —R(CH$_2$)$_d$C(C[hexose])$_g$(CH$_3$)$_{g-3}$, or —R(CH$_2$)$_d$C(C[pentose])$_g$(CH$_3$)$_{g-3}$, wherein g is an integer from 1 to 3, inclusive. In a further embodiment, g is an integer from 2 to 3, inclusive.

A peptidyl moiety comprises two or more amino acid residues joined by an amide (peptidyl) linkage between a carboxyl carbon of one amino acid and an amine nitrogen of another. An amino acid is any molecule having a carbon atom bonded to all of (a) a carboxyl carbon (which may be referred to as the "C-terminus"), (b) an amine nitrogen (which may be referred to as the "N-terminus"), (c) a hydrogen, and (d) a hydrogen or an organic moiety. The organic moiety can be termed a "side chain." The organic moiety can be further bonded to the amine nitrogen (as in the naturally occurring amino acid proline) or to another atom (such as an atom of the fullerene, among others), but need not be further bonded to any atom. The carboxyl carbon, the amine nitrogen, or both can be bonded to atoms other than those to which they are bonded in naturally-occurring peptides and the amino acid remain an amino acid according to the above definition.

The structures, names, and abbreviations of the names of the naturally-occurring amino acids are well known. See any college-level biochemistry textbook, such as Rawn, "Biochemistry," Neil Patterson Publishers, Burlington, N.C. (1989), among others. As is known, the vast majority of the naturally-occurring amino acids are chiral (can exist in two forms which are mirror images of each other). The prefix "D-" before a three-letter abbreviation for an amino acid indicates the amino acid residue has the "D-" chirality, and the prefix "L-" before a three-letter abbreviation for an amino acid indicates the amino acid residue has the "L-" chirality.

An amino acid residue is the unit of peptide formed by amidations at either or both the amine nitrogen and the carboxyl carbon of the amino acid. When a peptide sequence is defined solely with the names or abbreviations of amino acid residues, the peptide sequence will have a structure wherein, when reading from left to right, the N-terminus of the peptide will be at the left and the C-terminus of the peptide will be at the right. For example, in the peptide sequence "Glu-Met-Ser," the N-terminus of the peptide sequence will be at Glu and the C-terminus will be at Ser. The N-terminus can be a free amine or protonated amine group or can be involved in a bond with another atom or atoms, and the C-terminus can be a free carboxylic acid or carboxylate group or can be involved in a bond with another atom or atoms.

Examples of amino acids include, but are not limited to, those encoded by the genetic code or otherwise found in nature, among others. In one embodiment, the organic moiety of the amino acid can comprise the fullerene, optionally with a linker between the amino acid carbon and the fullerene.

Examples of peptides include, but are not limited to, naturally-occurring signaling peptides (peptides which are guided to specific organs, tissues, cells, or subcellular locations without intervention by a user), naturally-occurring proteins (peptides comprising at least 20 amino acid residues), and naturally-occurring enzymes (proteins which are capable of catalyzing a chemical reaction), among others.

In addition the amino acids, the peptidyl moiety can comprise other atoms. The other atoms can include, but are not limited to, carbon, nitrogen, oxygen, sulfur, silicon, or two or more thereof, among others. In one embodiment, at least some of the other atoms form a linker between the amino acid residues of the peptidyl moiety and the fullerene core. The linker can comprise from 1 to about 20 atoms, such as from 1 to about 10 carbon atoms. In one embodiment, at least some of the other atoms form a linker between one or more blocks of amino acid residues and one or more other blocks of amino acid residues. In one embodiment, at least some of the other atoms form a cap of the block of amino acid residues distal to the fullerene core. In one embodiment, at least some of the other atoms are bonded to the side chain of one or more amino acid residues. Any or all of the foregoing embodiments, among others, can be present in any peptidyl moiety.

In one embodiment, each peptidyl moiety can be independently selected from —C(=O)O—(CH$_2$)$_3$—C(=O)-alanine, —C(=O)O—(CH$_2$)$_3$—C(=O)-alanine-phenylalanine, or —C(=O)O—(CH$_2$)$_3$—C(=O)-alanine-alanine.

In one embodiment, each peptidyl moiety can be independently selected from Z-D-Phe-L-Phe-Gly, Z-L-Phe, Z-Gly-L-Phe-L-Phe, Z-Gly-L-Phe, Z-L-Phe-L-Phe, Z-L-Phe-L-Tyr, Z-L-Phe-Gly, Z-L-Phe-L-Met, Z-L-Phe-L-Ser, Z-Gly-L-Phe-L-Phe-Gly, wherein Z is a carbobenzoxy group.

Similarly, but independently, in one embodiment X can be selected from —H; —COOH; —CONH$_2$; —CONHR'; —CONR'$_2$; —COOR'; —CHO; —(CH$_2$)$_d$OH; a peptidyl moiety; a heterocyclic moiety; a branched moiety comprising one or more terminal —OH, —NH$_2$, triazole, tetrazole, or sugar groups; or a salt thereof. In one embodiment, X$^2$ can be selected from —R, —RCOOH, —RCONH$_2$, —RCONHR', —RCONR'$_2$, —RCOOR', —RCHO, —R(CH$_2$)$_d$OH, a peptidyl moiety, or a salt thereof. In one embodiment, X$^2$ can be selected from —H; —COOH; —CONH$_2$; —CONHR'; —CONR'$_2$; —COOR'; —CHO; —(CH$_2$)$_d$OH; a peptidyl moiety; —R; —RCOOH; —RCONH$_2$; —RCONHR'; —RCONR'$_2$; —RCOOR'; —RCHO; —R(CH$_2$)$_d$OH; a heterocyclic moiety; a branched moiety comprising one or more terminal —OH, —NH$_2$, triazole, tetrazole, or sugar groups; or a salt thereof.

In this embodiment, when m is 3, at least one X$^1$ or X$^2$ is not —COOH.

A substituted fullerene can exist in one or more isomers. All structural formulas shown herein are not to be construed as limiting the structure to any particular isomer.

All possible isomers of the substituted fullerenes disclosed herein are within the scope of the present disclosure. For example, in >CX$^1$X$^2$, one group (X$^1$ or X$^2$) of each substituent points away from the fullerene core, and the other group points toward the fullerene core. Continuing the example, the central carbon of each substituent group (by which is meant the carbon with two bonds to the fullerene core, one bond to X$^1$, and one bond to X$^2$) is chiral when X$^1$ and X$^2$ are different.

It will also be apparent that substituted fullerenes having two or more substituent groups will have isomers resulting from the different possible sites of bonding of the substituent groups to the fullerene core.

In one embodiment, the substituted fullerene is a decarboxylation product of (C$_{60}$(>C(COOH)$_2$)$_3$) (C3). By "decarboxylation product of C3" is meant the product of a reaction wherein 0 or 1 carboxy (—COOH) groups are removed from each of the three malonate moieties (>C(COOH)$_2$) of C3 and replaced with —H, provided at least one of the malonate moieties has 1 carboxy group replaced with —H. This can be considered as the loss of CO$_2$ from a malonate moiety. Decarboxylation can be performed by heating C3 in acid, among other techniques.

During decarboxylation of C3, only CO$_2$ loss from C3 is observed; each malonate moiety retains at least one carboxyl; and the decarboxylation stops at loss of 3 CO$_2$ groups, one from each malonate moiety of C3. The skilled artisan having the benefit of the present disclosure will recognize that substituted fullerenes having 1, 2, 4, 5, or 6 malonate moieties would also undergo decarboxylation.

In C3, each malonate moiety has a carboxy group pointing to the outside (away from the fullerene), which we herein term exo, and a carboxy group pointing to the inside (toward the fullerene), which we herein term endo. FIG. 1A presents a structural formula of C3.

Figure 2:
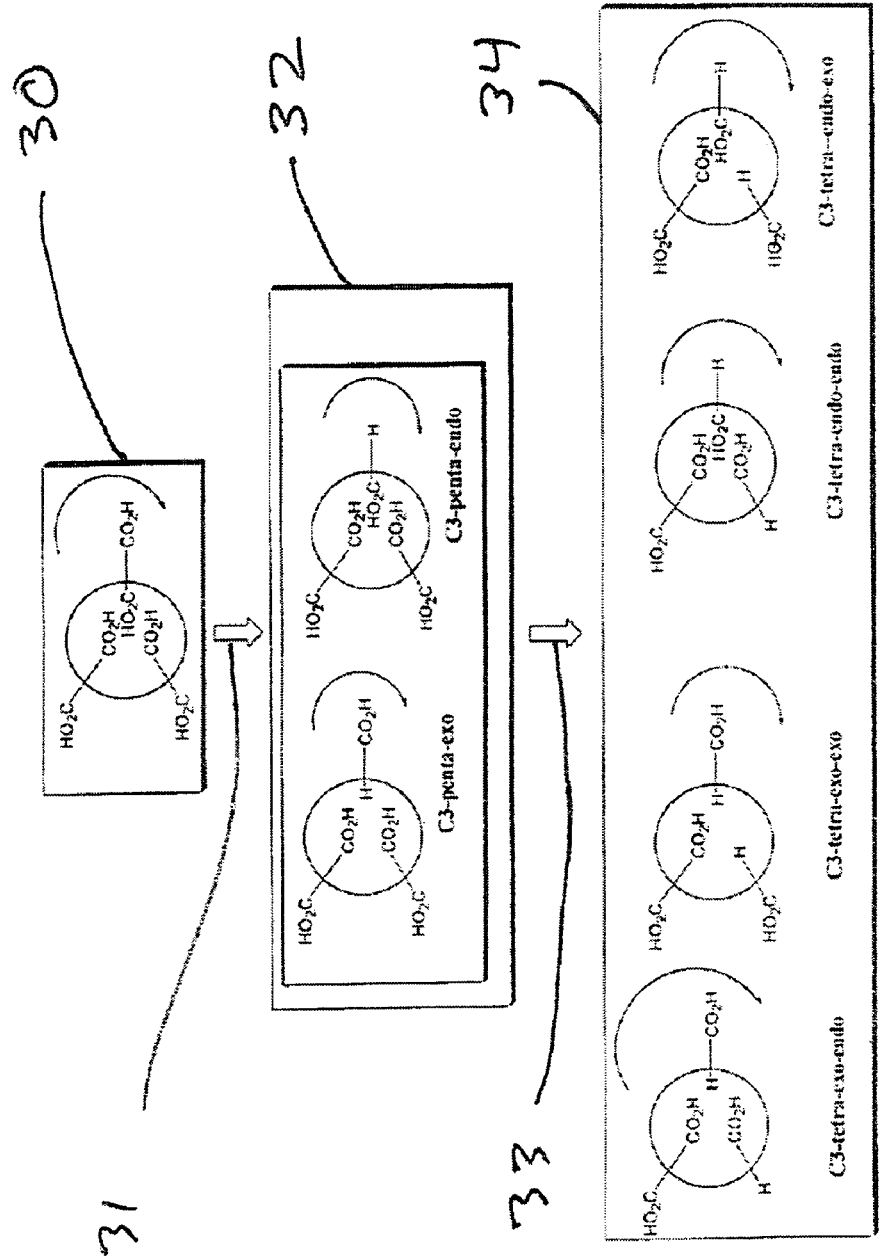
FIG. 2 shows the decarboxylation of C3 to C3-penta-acid and thence to C3-tetra-acid.

FIG. 2 shows C3 (in box 30) and the products of subsequent loss via decarboxylation of one or two CO$_2$ groups, giving C3-penta-acids (in box 32) and C3-tetra-acids (in box 34). Decarboxylation is represented by the open arrows 31 and 33; the isomers of C3, C3-penta-acid, and C3-tetra-acid are shown in box 30, in box 32, and in box 34, respectively.

In the interest of precise nomenclature, we define the order of exo or endo by always naming the groups in a clockwise manner.

Figure 3:
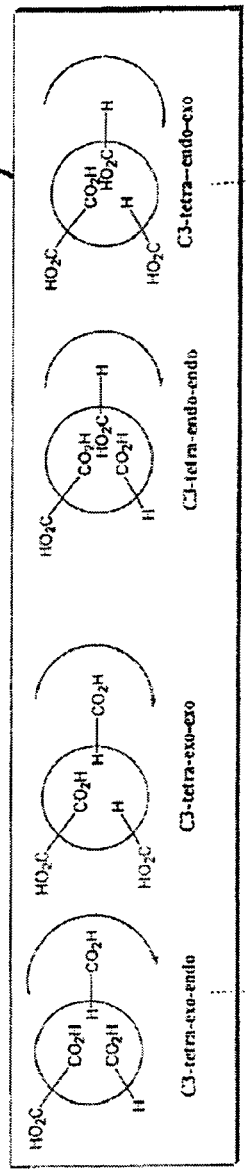
FIG. 3 shows the decarboxylation of C3-tetra-acid to C3-tris-acid.
Figure 3:
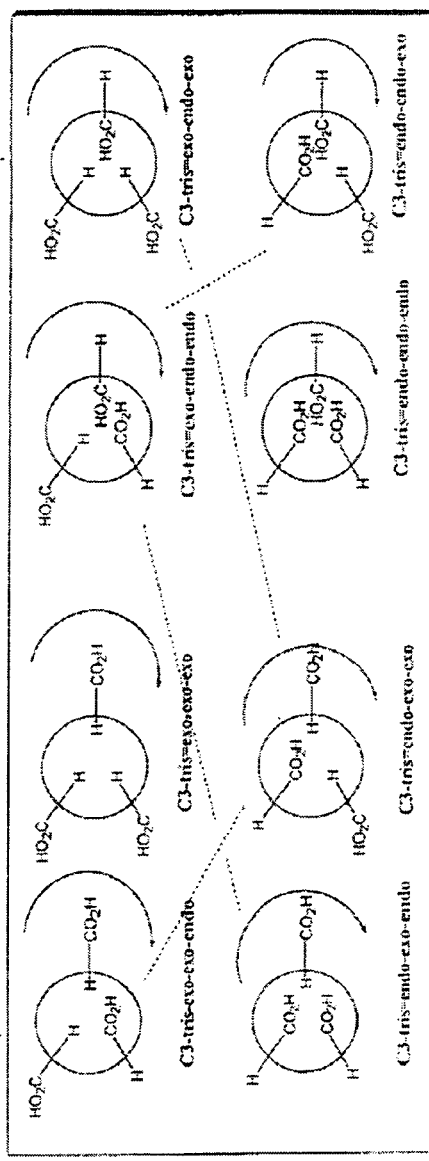

FIG. 3 shows the products of subsequent loss via decarboxylation of a third CO$_2$ group from the C3-tetra-acids shown in box 34, giving C3-tris-acids (box 42). Decarboxylation is represented by the open arrow 41; the isomers of C3-tetra-acid and C3-penta-acid are shown in box 34 and in box 42, respectively. Isomers that differ only by rotation are connected by dashed lines 43, 44, and 45.

Figure 4:
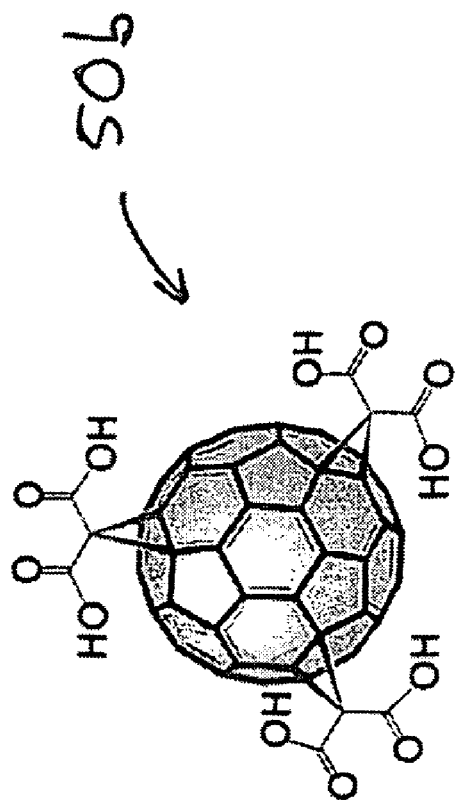
FIG. 4 shows the chirality of C3.
Figure 4:
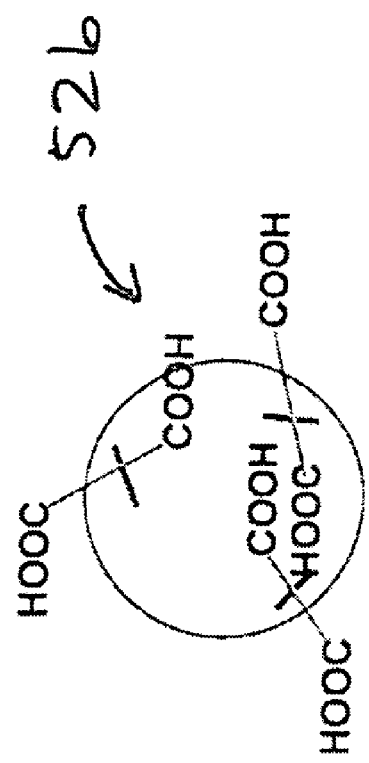
Figure 4:
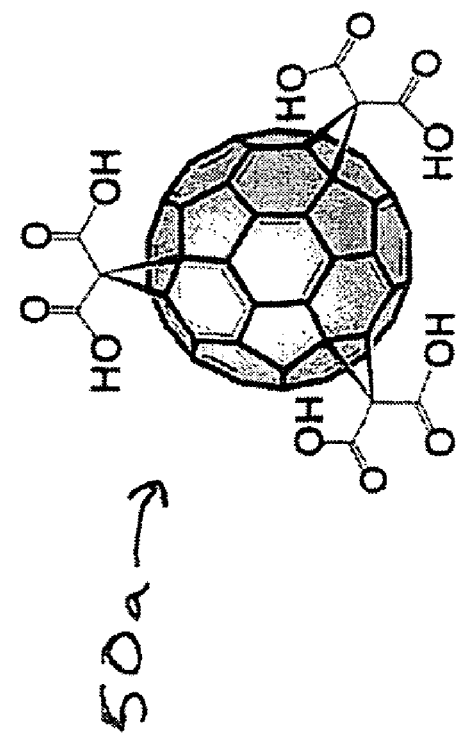
Figure 4:
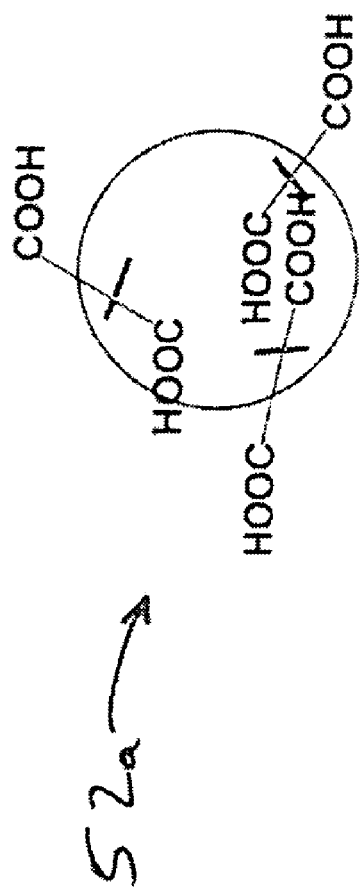
Figure 5:
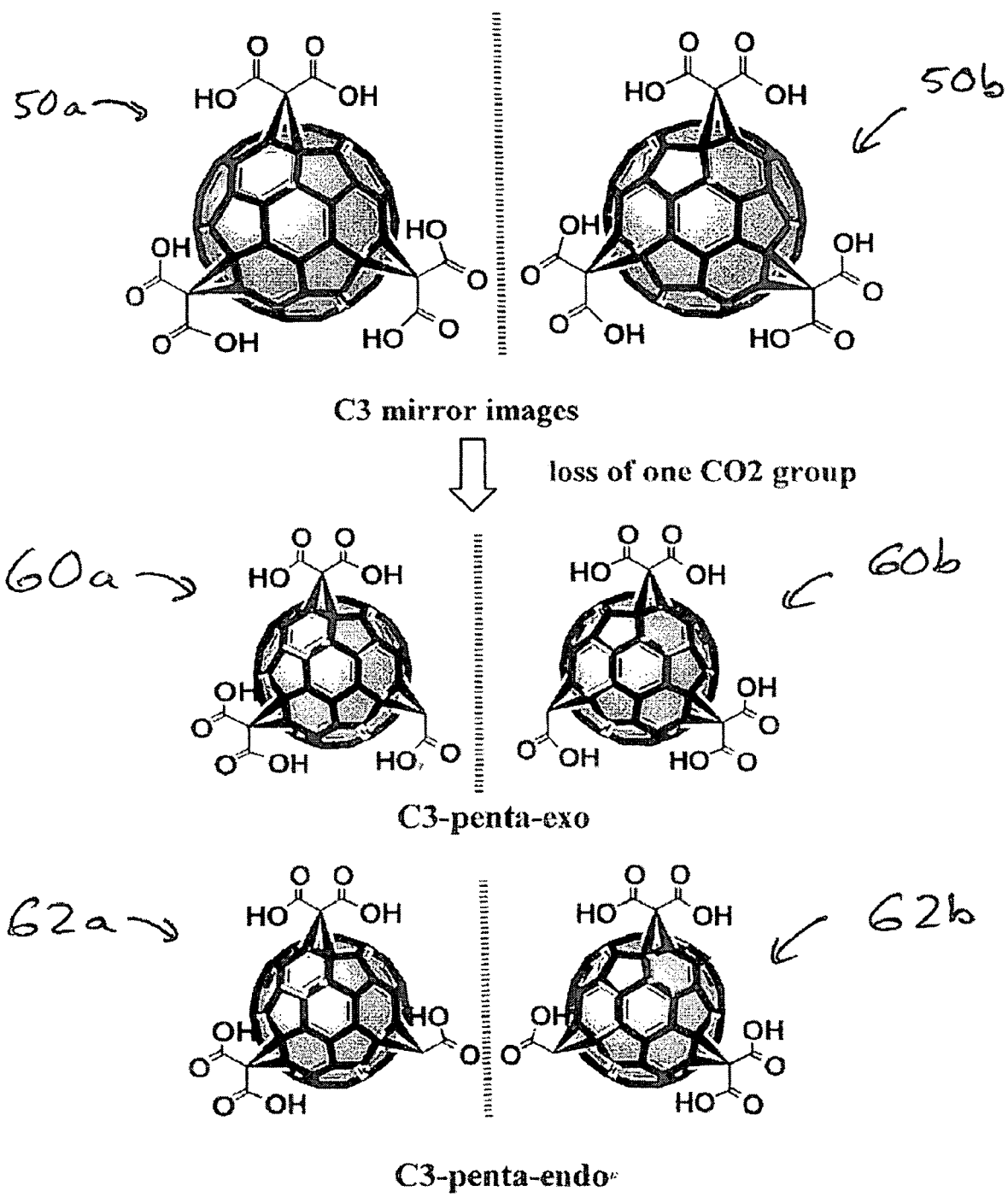
FIG. 5 shows the effect of C3 chirality on isomers formed by decarboxylation.

FIG. 4 shows the chirality of C3, both in a structural formula (mirror images 50*a* and 50*b*) and a schematic representation (mirror images 52*a* and 52*b*). FIG. 5 shows the chirality of C3-penta-acids (mirror images 60*a* and 60*b*; mirror images 62*a* and 62*b*).

Figure 6:
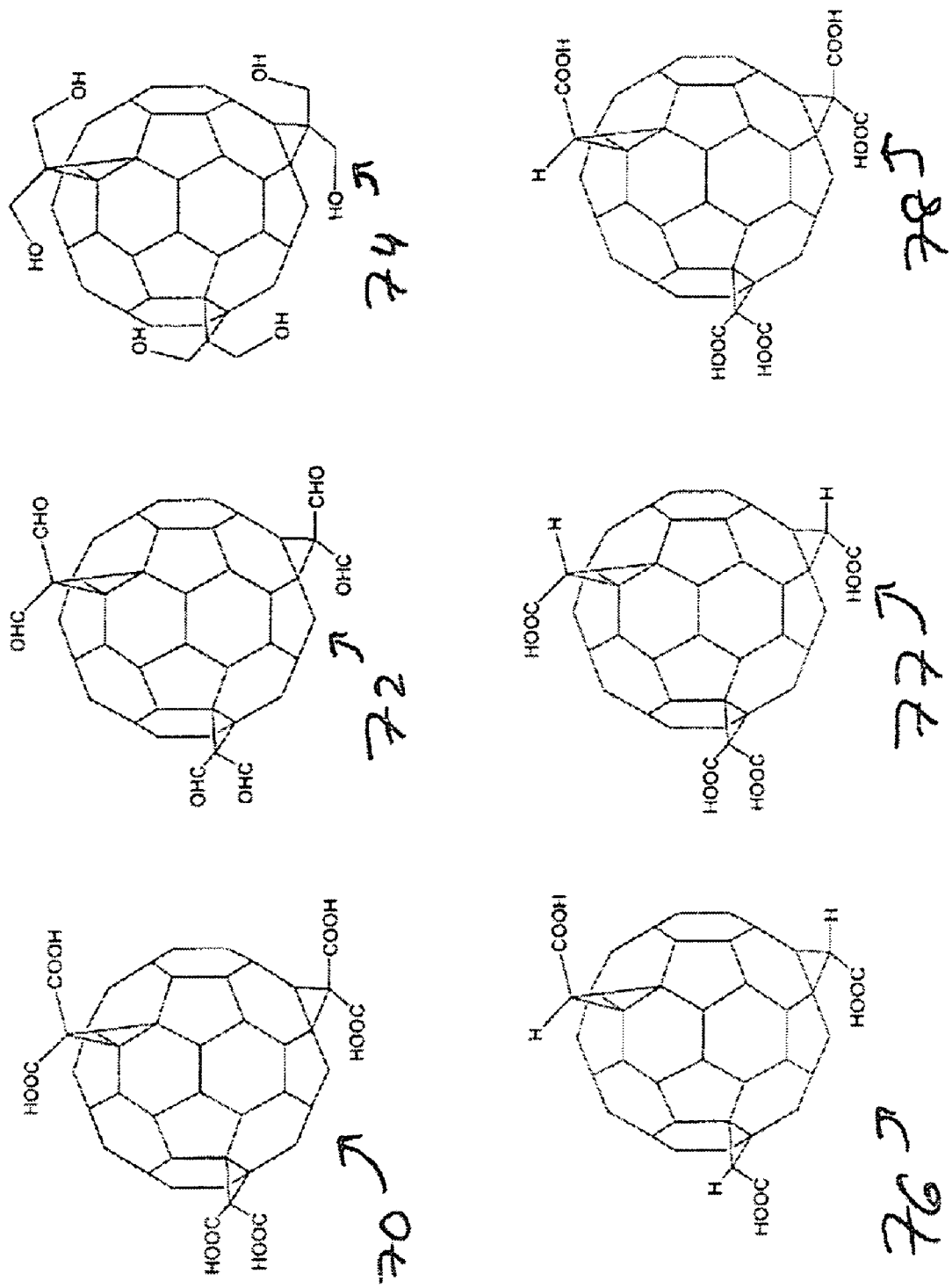
FIG. 6 shows exemplary substituted fullerenes according to one embodiment of the present invention. C3, in the upper left, is comparative.

In another embodiment, the substituted fullerene comprises one of the structures 72, 74, 76, 77, or 78 shown in FIG. 6.

In one embodiment, the substituted fullerene comprises $C_{60}$ and 3 ($>CX^1X^2$) groups in the C3 orientation (e.g., the orientation of the substituents shown in structural formula 50*a* in FIG. 4) or the D3 orientation (e.g., the orientation of the substituents shown in structural formula 50*b* in FIG. 4). The D3 orientation is a mirror translation of the C3 orientation (e.g., structural formula 50*b* in FIG. 4). The above description of C3-penta-acids, C3-tetra-acids, and C3-tris-acids also applies to D3 orientations of penta acids, tetra acids, and tris acids.

In one embodiment, as shown in FIG. 10, the substituted fullerene comprises $C_{60}$ and 2 ($>CX^1X^2$) groups in the trans-2 orientation 1206, the trans-3 orientation 1207, the e orientation 1208, or the cis-2 orientation 1209.

In another embodiment, also as shown in FIG. 10, the substituted fullerene comprises $C_{70}$ and 2 ($>CX^1X^2$) groups in the bis orientation 1210 or 1211.

Figure 7B:
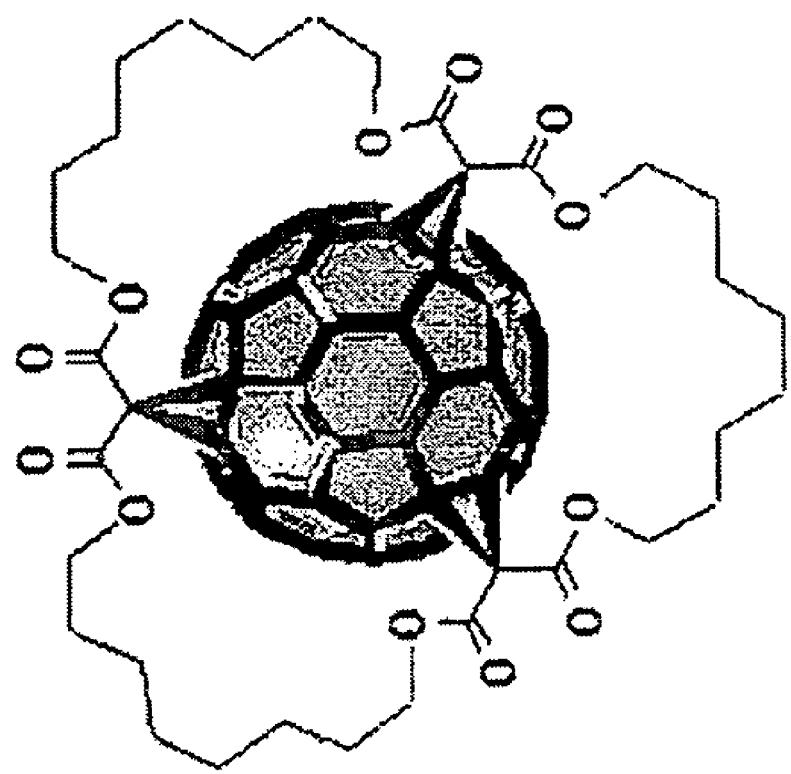
FIGS. 7A and 7B show two exemplary substituted fullerenes.
Figure 7A:
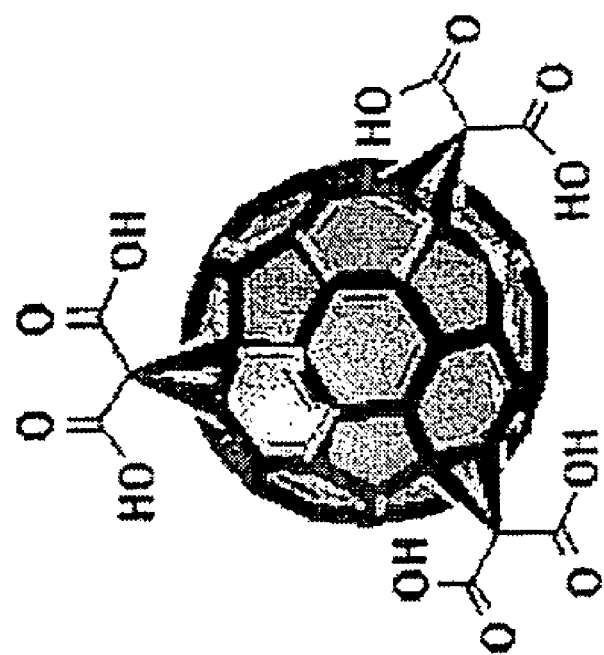

In another embodiment, the substituted fullerene has the structure shown in FIG. 7B.

In one embodiment, the substituted fullerene comprises a fullerene core (Cn) and from 1 to 18 —$X^3$ groups bonded to the fullerene core. The notation "—$X^3$" indicates the group is bonded to the fullerene core by a single bond between one atom of the $X^3$ group and one carbon atom of the fullerene core. In specific $X^3$ groups referred to below, any unfilled valences represent the single bond between the group and the fullerene core.

In one embodiment, the substituted fullerene comprises from 1 to about 6 —$X^3$ groups and each —$X^3$ group is independently selected from:

—$N^+(R^2)(R^3)(R^4)$, wherein $R^2$, $R^3$, and $R^4$ are independently —H or —$(CH_2)_d$—$CH_3$, wherein d is an integer from 0 to about 20;

—$N+(R^2)(R^3)(R^8)$, wherein $R^2$ and $R^3$ are independently —H or —$(CH_2)_d$—$CH_3$, wherein d is an integer from 0 to about 20, and each $R^8$ is independently —$(CH_2)_f$—$SO_3^-$, —$(CH_2)_f$—$PO_4^-$, or —$(CH_2)_f$—$COO^-$, wherein f is an integer from 1 to about 20;

—$C(R^5)(R^6)(R^7)$, wherein $R^5$, $R^6$, and $R^7$ are independently —COOH, —H, —CH(=O), —$CH_2OH$, or a peptidyl moiety;

—$C(R^2)(R^3)(R^8)$, wherein $R^2$ and $R^3$ are independently —H or —$(CH_2)_d$—$CH_3$, wherein d is an integer from 0 to about 20, and each $R^8$ is independently —$(CH_2)_f$—$SO_3^-$, —$(CH_2)_f$—$PO_4^-$, or —$(CH_2)_f$—$COO^-$, wherein f is an integer from 1 to about 20;

—$(CH_2)_e$—COOH, —$(CH_2)_e$—$CONH_2$, or —$(CH_2)_e$—COOR', wherein e is an integer from 1 to about 6 and each R' is independently (i) a hydrocarbon moiety having from 1 to about 6 carbon atoms, (ii) an aryl-containing moiety having from 6 to about 18 carbon atoms, (iii) a hydrocarbon moiety having from 1 to about 6 carbon atoms and a terminal carboxylic acid or alcohol, or (iv) an aryl-containing moiety having from 6 to about 18 carbon atoms and a terminal carboxylic acid or alcohol;

a peptidyl moiety; or, an aromatic heterocyclic moiety containing a cationic nitrogen.

As will be apparent from the foregoing, a substituted fullerene according to this embodiment can comprise one or more groups selected from one or more of the foregoing categories.

In another embodiment, the substituted fullerene comprises a fullerene core (Cn) and from 1 to 6 —$X^4$— groups bonded to the fullerene core. The notation "—$X^4$—" indicates the group is bonded to the fullerene core by two single bonds, wherein one single bond is between a first atom of the group and a first carbon of the fullerene core, and the other single bond is between a second atom of the group and a second carbon of the fullerene core. (The adjectives "first" and "second," wherever they appear herein, do not imply a particular ordering, in time, space, or both, of the nouns modified by the adjectives).

In one embodiment, each —$X^4$— group is independently

wherein $R^2$ is independently —H or —$(CH_2)_d$—$CH_3$, wherein d is an integer from 0 to about 20, and $R^8$ is independently —$(CH_2)_f$—$SO_3^-$, —$(CH_2)_f$—$PO_4^-$, or —$(CH_2)_f$—$COO^-$, wherein f is an integer from 1 to about 20.

In another embodiment, each —$X^4$— group is independently

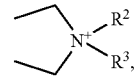

wherein each $R^2$ and $R^3$ is independently —H or —$(CH_2)_d$—$CH_3$, wherein d is an integer from 0 to about 20.

In another embodiment, each —$X^4$— group is independently selected from:

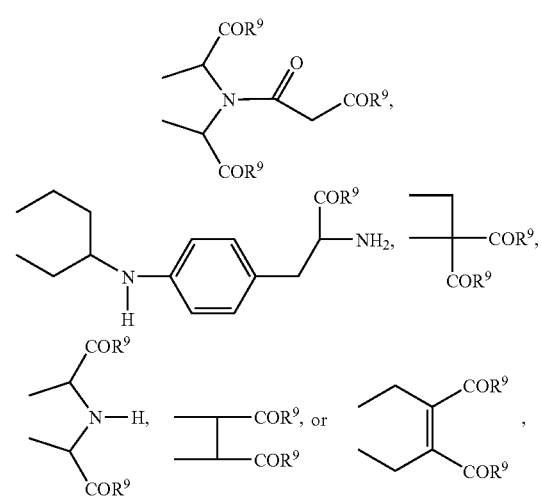

wherein each $R^2$ is independently —H or —$(CH_2)_d$—$CH_3$, wherein d is an integer from 0 to about 20, and each R⁹ is independently —H, —OH, —OR', —NH₂, —NHR', —NHR'₂, or —(CH₂)$_d$OH, wherein each R' is independently (i) a hydrocarbon moiety having from 1 to about 6 carbon atoms, (ii) an aryl-containing moiety having from 6 to about 18 carbon atoms, (iii) a hydrocarbon moiety having from 1 to about 6 carbon atoms and a terminal carboxylic acid or alcohol, or (iv) an aryl-containing moiety having from 6 to about 18 carbon atoms and a terminal carboxylic acid or alcohol.

In one embodiment of the present invention, the substituted fullerene comprises a fullerene core (Cn), and from 1 to 6 dendrons bonded to the fullerene core.

A dendron within the meaning of the invention is an addendum of the fullerene which has a branching at the end as a structural unit. Dendrons can be considered to be derived from a core, wherein the core contains two or more reactive sites. Each reactive site of the core can be considered to have been reacted with a molecule comprising an active site (in this context, a site that reacts with the reactive site of the core) and two or more reactive sites, to define a first generation dendron. First generation dendrons are within the scope of the term "dendron," as used herein. Higher generation dendrons can be considered to have formed by each reactive site of the first generation dendron having been reacted with the same or another molecule comprising an active site and two or more reactive sites, to define a second generation dendron, with subsequent generations being considered to have been formed by similar additions to the latest generation. Although dendrons can be formed by the techniques described above, dendrons formed by other techniques are within the scope of "dendron" as used herein.

The core of the dendron is bonded to the fullerene by one or more bonds between (a) one or more carbons of the fullerene and (b) one or more atoms of the core. In one embodiment, the core of the dendron is bonded to the fullerene in such a manner as to form a cyclopropanyl ring.

In one embodiment, the core of the dendron comprises, between the sites of binding to the fullerene and the reactive sites of the core, a spacer, which can be a chain of 1 to about 100 atoms, such as about 2 to about 10 carbon atoms.

The generations of the dendron can comprise trivalent or polyvalent elements such as, for example, N, C, P, Si, or polyvalent molecular segments such as aryl or heteroaryl. The number of reactive sites for each generation can be about two or about three. The number of generations can be between 1 and about 10, inclusive.

More information regarding dendrons suitable for adding to fullerenes can be found in Hirsch, U.S. Pat. No. 6,506,928, the disclosure of which is hereby incorporated by reference.

Figure 8A:
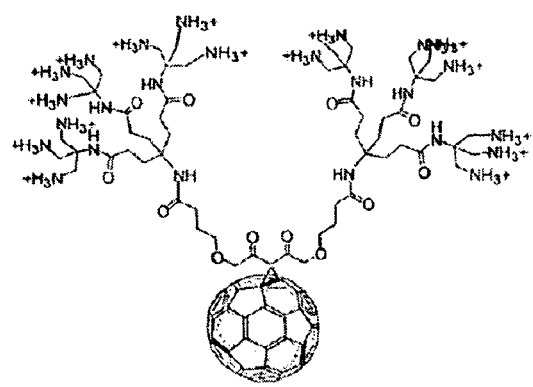
FIGS. 8A–8G show seven exemplary dendrofullerenes.
Figure 8B:
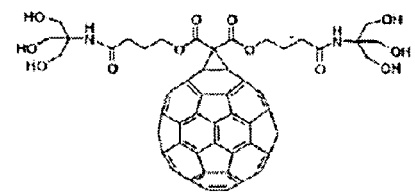
Figure 8C:
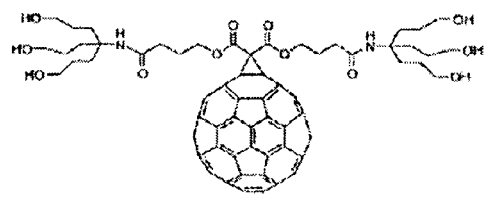
Figure 8D:
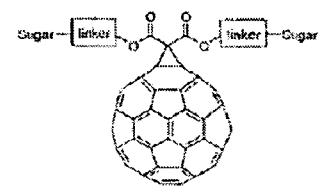
Figure 8E:
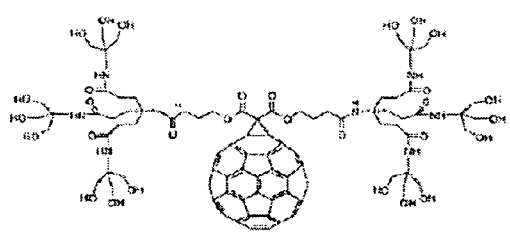
Figure 8F:
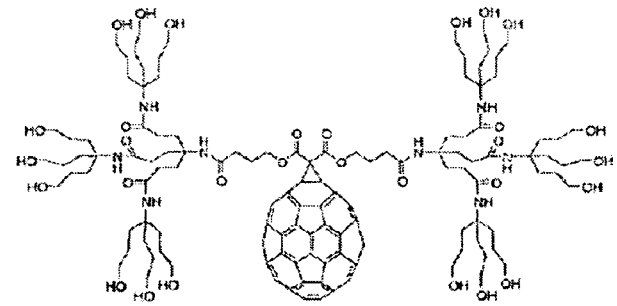
Figure 8G:
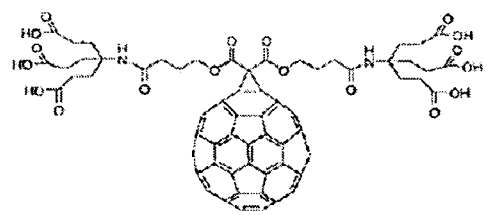
Figure 9:
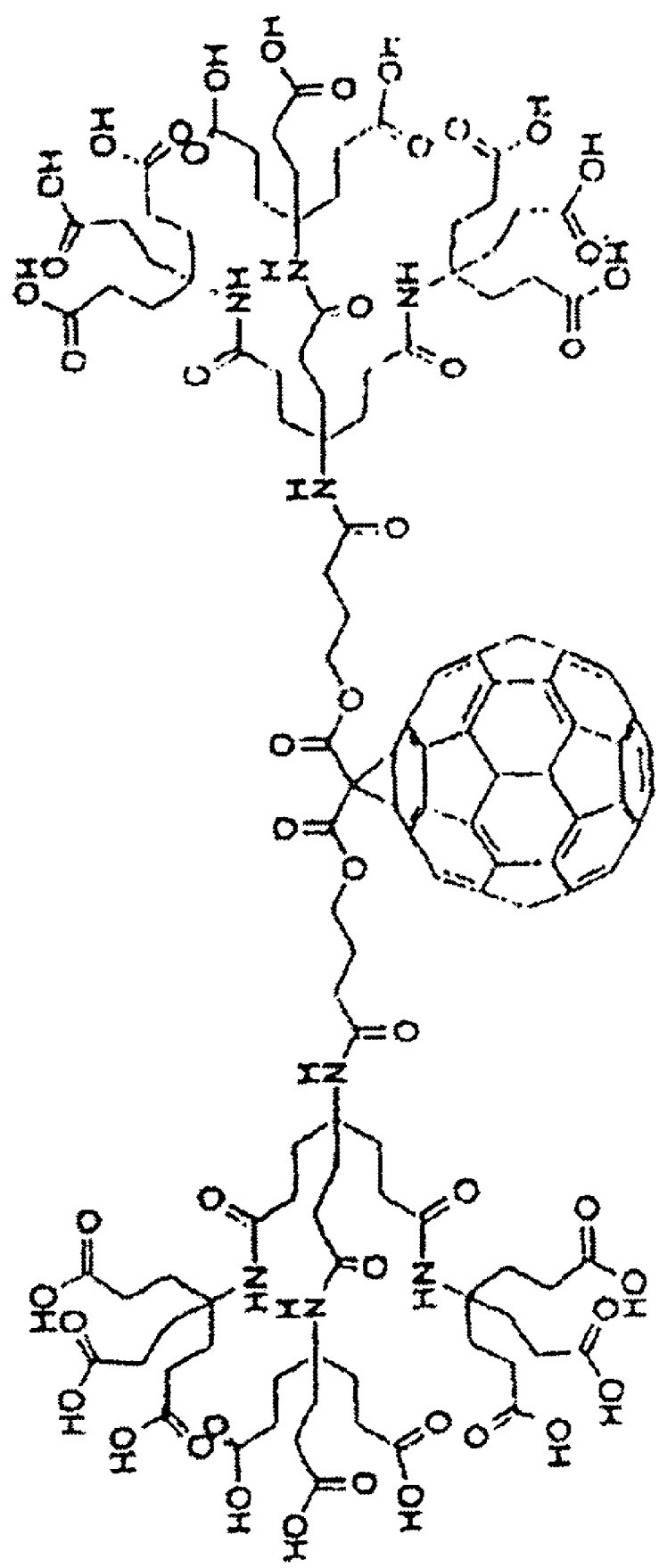
FIG. 9 shows dendrofullerene DF-1.
Figure 10A:
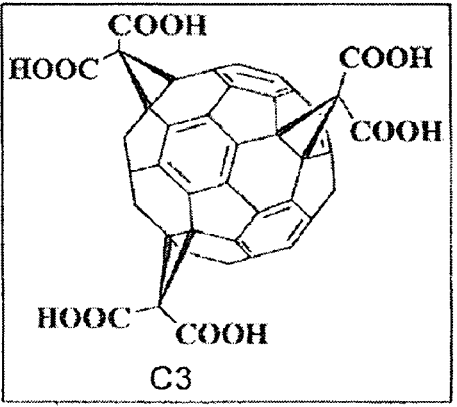
Figure 10A:
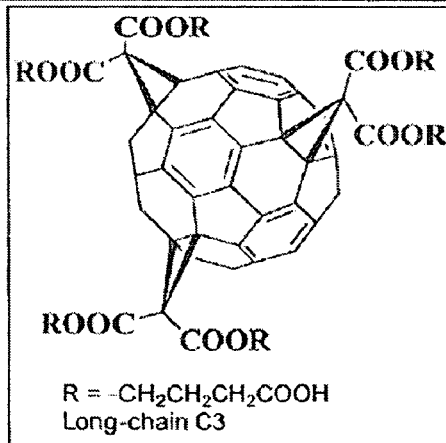
Figure 10B:
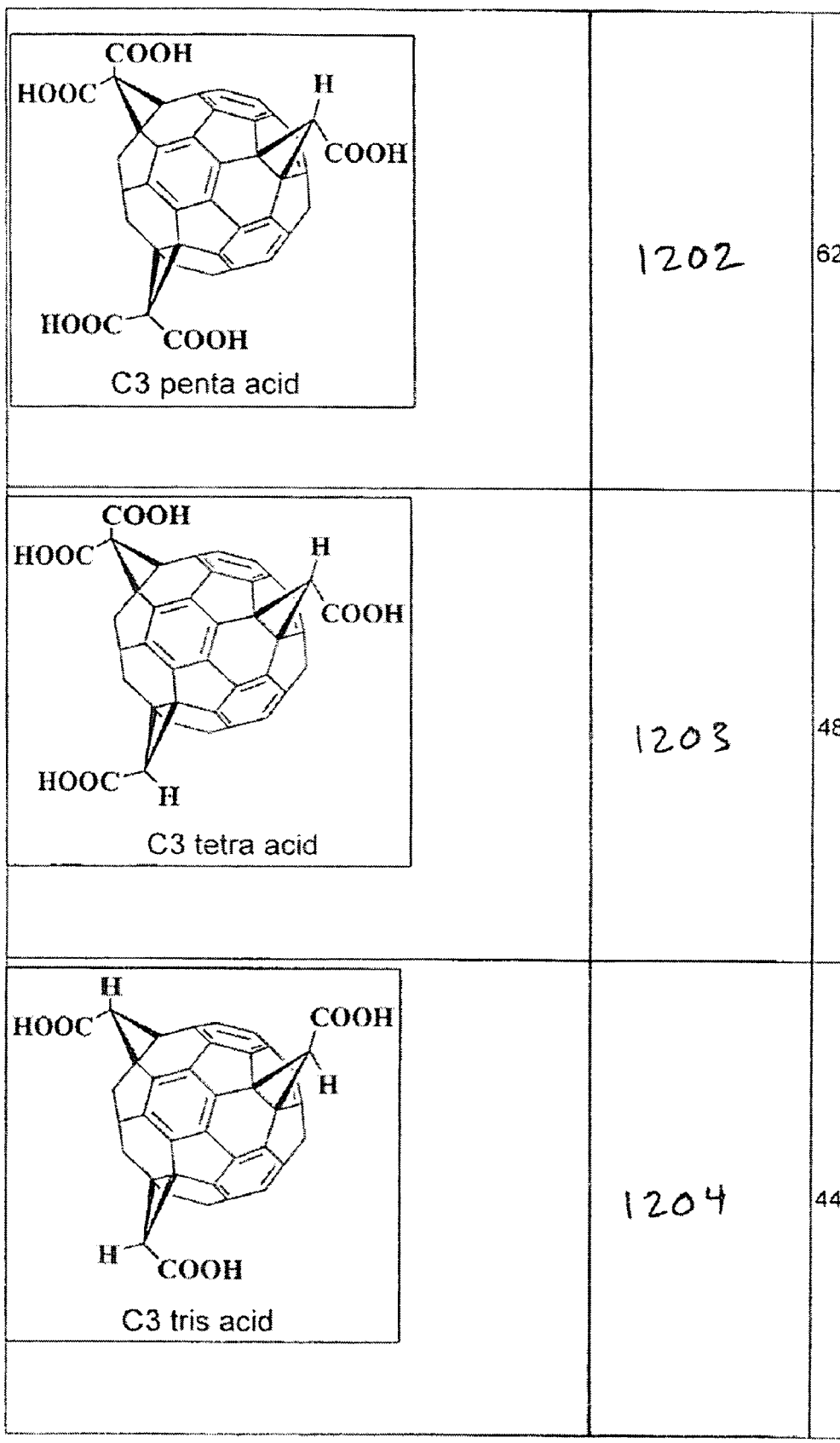
Figure 10C:
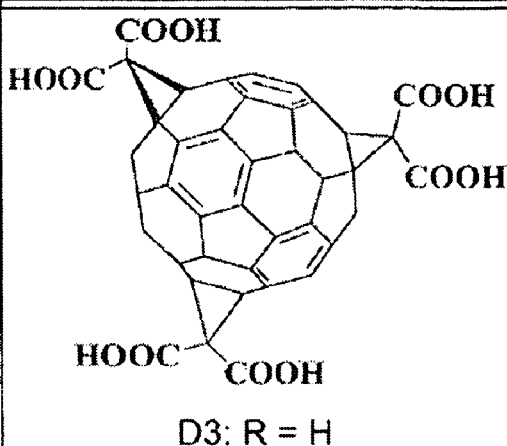
Figure 10C:
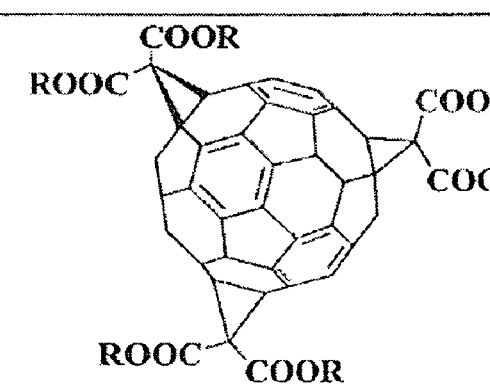
Figure 10C:
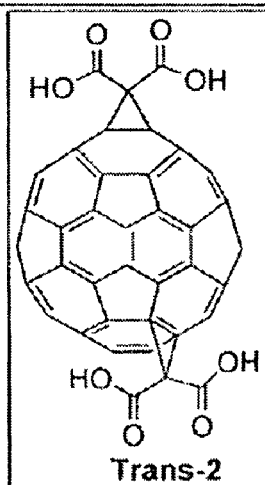
Figure 10D:
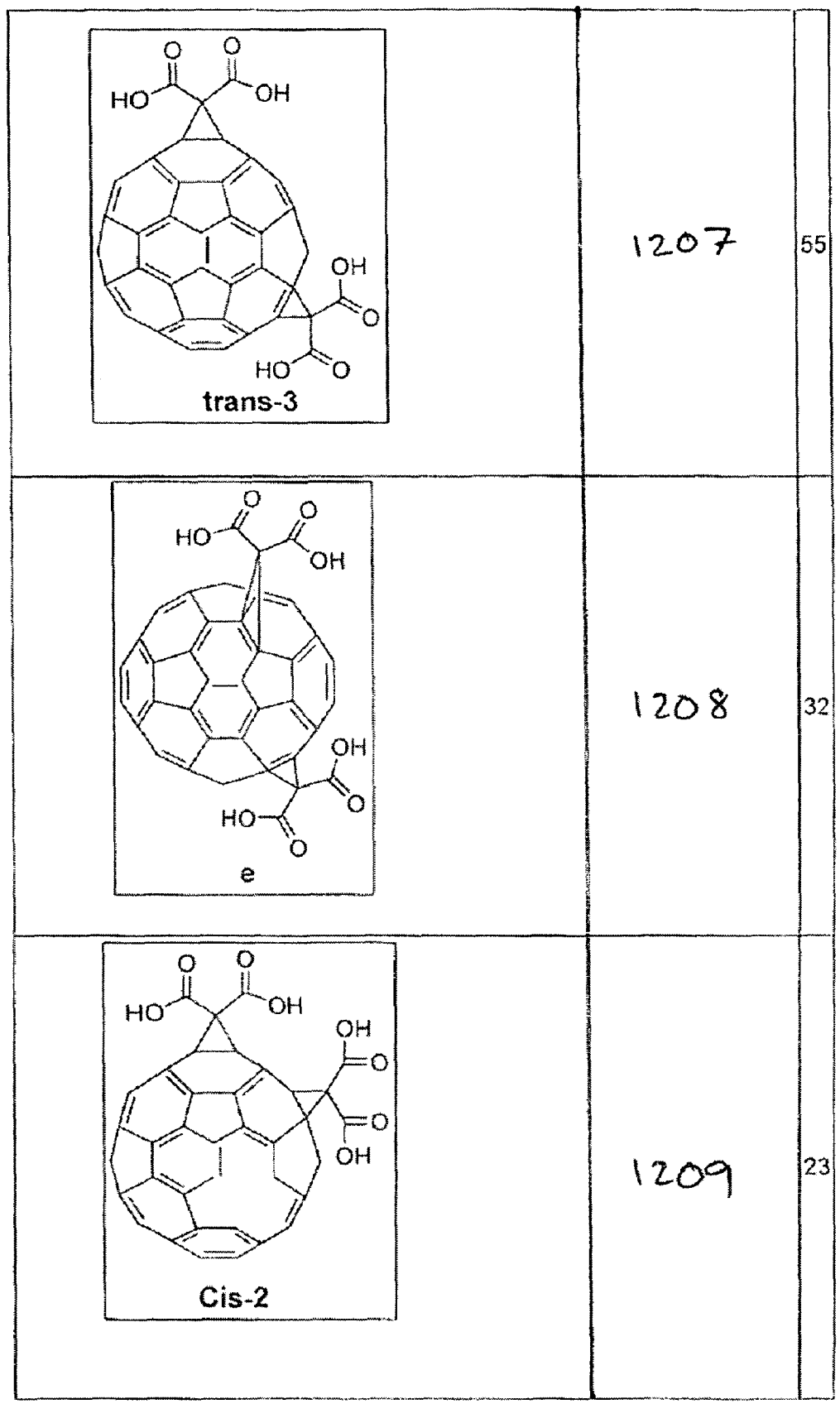
Figure 10E:
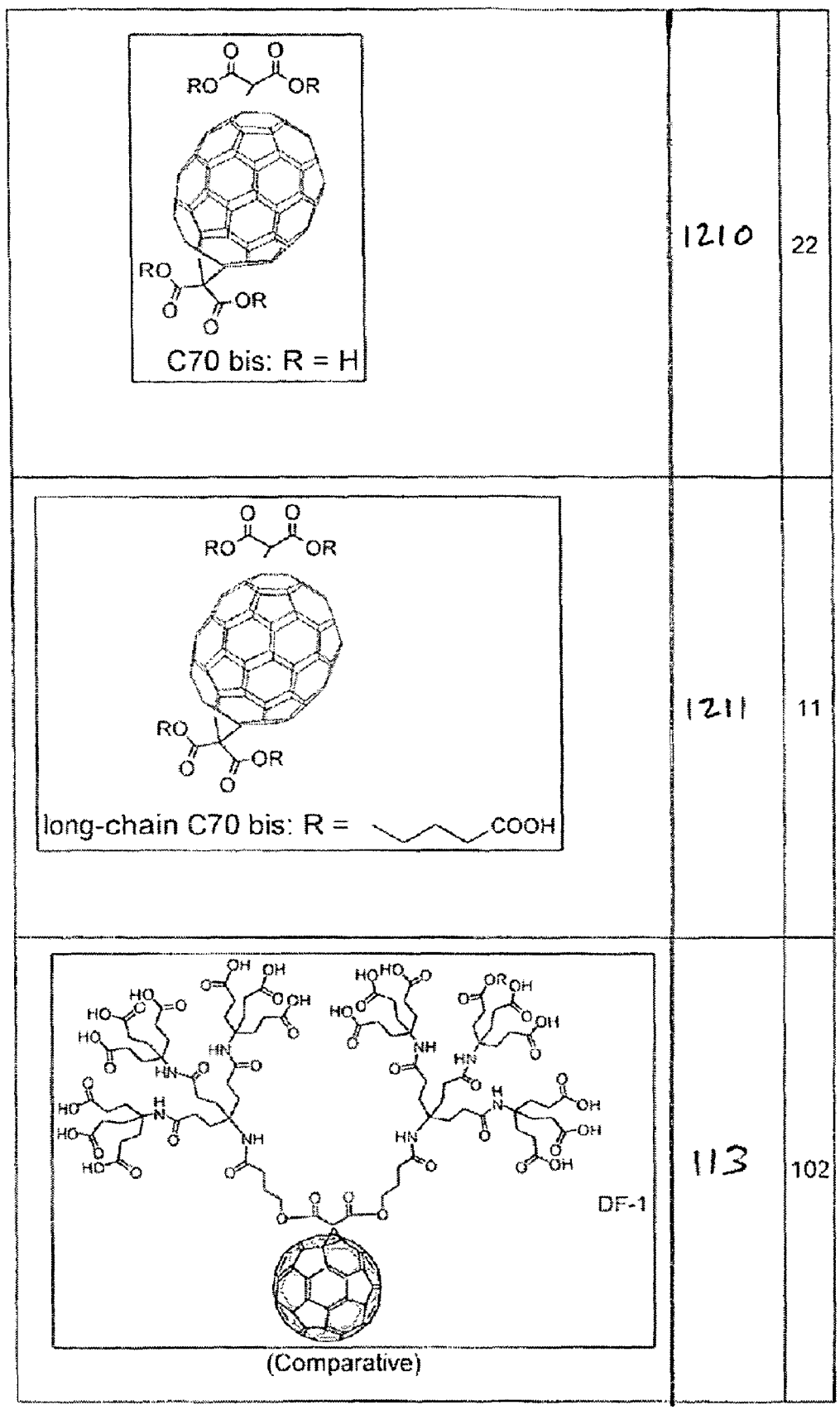
Figure 10F:
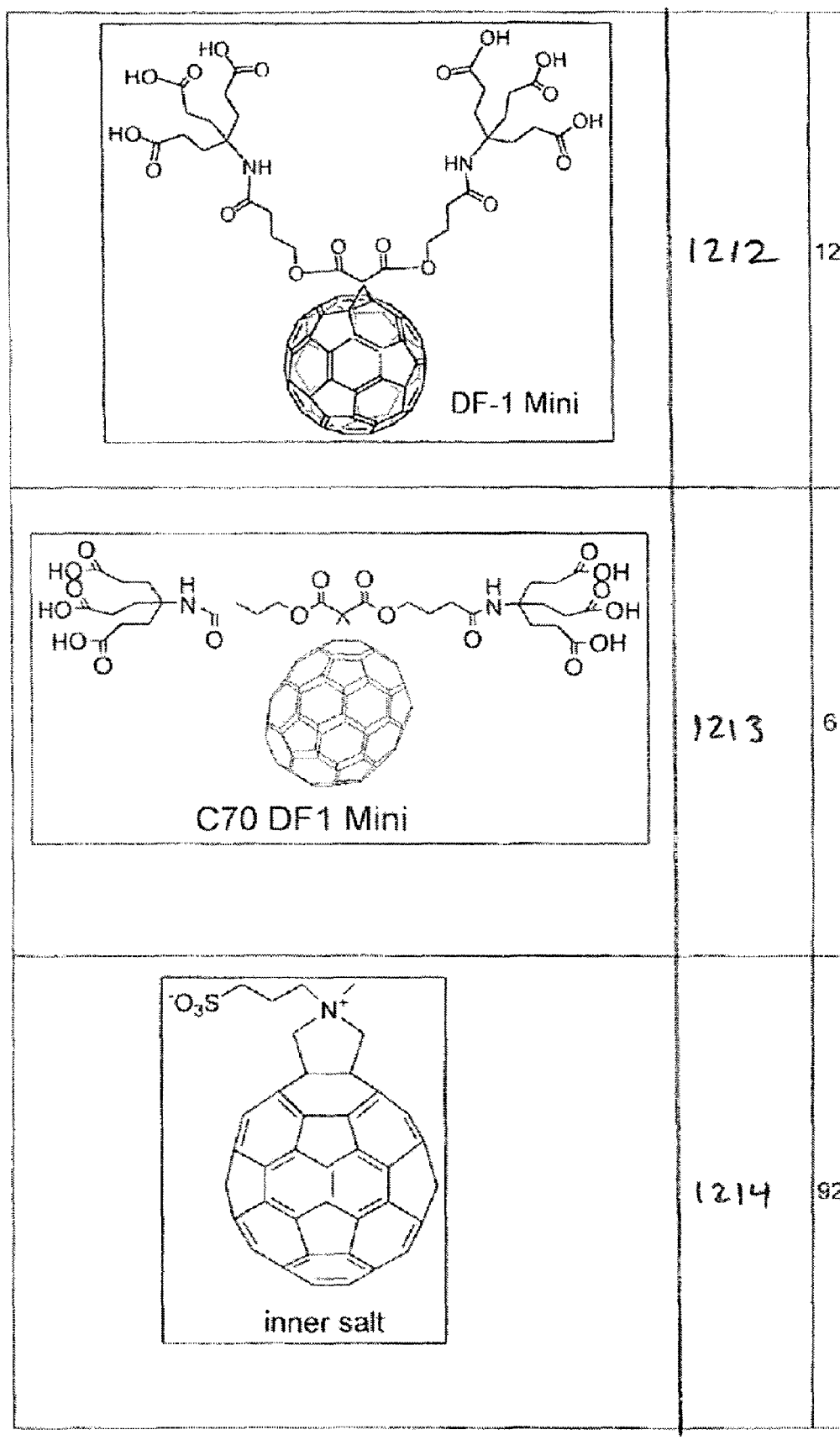
Figure 10G:
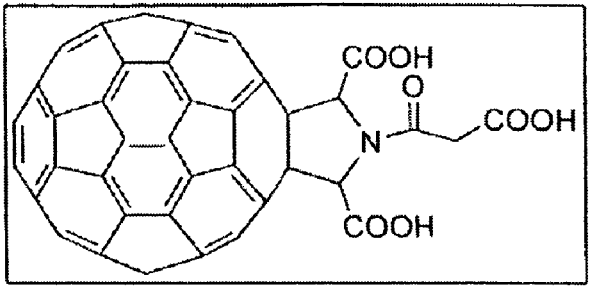

In a further embodiment, the substituted fullerene has a structure selected from FIGS. 8A–8G. In FIG. 8D, each "Sugar" independently represents a carbohydrate moiety, and each "linker" independently represents an organic or inorganic moiety. In a further embodiment, each Sugar is independently ribose or deoxyribose, and each "linker" independently has the formula —(CH₂)$_d$—, wherein d is an integer from 0 to about 20.

The substituted fullerene of this embodiment can further comprise a nondendron moiety, which is an addendum to a fullerene, wherein the addendum does not have a core and generations structure as found in dendrons defined above. Exemplary nondendrons include, but are not limited to, —H; —COOH; —CONH₂; —CONHR'; —CONR'₂; —COOR'; —CHO; —(CH₂)$_d$OH; a peptidyl moiety; a heterocyclic moiety; a branched moiety comprising one or more terminal —OH, —NH₂, triazole, tetrazole, or sugar groups; or a salt thereof. When the substituted fullerene comprises one dendron which comprises 18 —COOH groups, the substituted fullerene comprises one or more nondendrons.

In another embodiment, a substituted fullerene of the present invention has a structure as defined above and an IC₅₀, according to the assay described in Example 1, below, of 100 μM or less.

The substituted fullerene of the present invention can satisfy one, two, or more of the foregoing embodiments, consistent with the plain meaning of "comprising."

A substituted fullerene of any of the foregoing embodiments can further comprise an endohedral metal. "Metal" means at least one atom of a metallic element, and "endohedral" means the metal is encaged by the fullerene core. The metal can be elemental, or it can be an atom or atoms in a molecule comprising other elements. A substituted fullerene comprising an endohedral metal can be termed a "metallofullerene." In a further embodiment, the metallofullerene can be represented by the structure:

$M_m@C_n$, wherein each M independently is a molecule containing a metal;

m is an integer from 1 to about 5; and $C_n$ is a fullerene core comprising n carbon atoms, wherein n is an integer equal to or greater than 60.

In one embodiment, M is a transition metal atom. In one embodiment, M is a metal atom with an atomic number greater than about 55. Exemplary metals include those which do not form metal carbides. In one embodiment, the metal is Ho, Gd, or Lu.

In one embodiment, M is an organometallic molecule or an inorganometallic molecule. In one embodiment, M is a molecule having the formula M'₃N, wherein each M' independently is a metal atom. Each metal atom M' can be any metal, such as a transition metal, a metal with an atomic number greater than about 55, or one of the exemplary metals given above, among others.

In one embodiment, M is a metal capable of reacting with a reactive oxygen species.

In one embodiment, the metallofullerene is characterized in that M is Ho, Ho₃N, Gd, Gd₃N, Lu, or Lu₃N; m is 1; and n is 60.

In one embodiment, the substituted fullerene is polymerized, by which is meant a plurality of fullerene cores are present in a single molecule. The molecule can comprise carbon-carbon bonds between a first fullerene core and a second fullerene core, covalent bonds between a first substituent group on a first fullerene core and a second substituent group on a second fullerene core, or both.

The substituted fullerene can be a component of a composition comprising one or more other components. In one embodiment, the composition further can comprise an amphiphilic fullerene having the formula $(B)_b$—$C_n$-$(A)_a$, wherein $C_n$ is a fullerene moiety comprising n carbon atoms, wherein n is an integer and 60≤n≤240; B is an organic moiety comprising from 1 to about 40 polar headgroup moieties; b is an integer and 1≤b≤5; each B is covalently bonded to the $C_n$ through 1 or 2 carbon-carbon, carbon-oxygen, or carbon-nitrogen bonds; A is an organic moiety comprising a terminus proximal to the $C_n$ and one or more termini distal to the $C_n$, wherein the termini distal to the $C_n$ each comprise —$C_xH_y$, wherein x is an integer and 8≤x≤24, and y is an integer and 1≤y≤2x+1; a is an integer, $1 \leq a \leq 5$; $2 \leq b+a \leq 6$; and each A is covalently bonded to the $C_n$ through 1 or 2 carbon-carbon, carbon-oxygen, or carbon-nitrogen bonds.

B can be chosen from any organic moiety comprising from 1 to about 40 polar headgroup moieties. A "polar headgroup" is a moiety which is polar, by which is meant that the vector sum of the bond dipoles of each bond within the moiety is nonzero. A polar headgroup can be positively charged, negatively charged, or neutral. The polar headgroup can be located such that at least a portion of the moiety can be exposed to the environment of the molecule. Exemplary polar headgroup moieties can include, but are not limited to, carboxylic acid, alcohol, amide, and amine moieties, among others known in the art. Preferably, B has from about 6 to about 24 polar headgroup moieties. In one embodiment, B has a structure wherein the majority of the polar headgroup moieties are carboxylic acid moieties, which are exposed to water when the amphiphilic fullerene is dissolved in an aqueous solvent. A dendrimeric or other regular highly-branched structure is suitable for the structure of B.

The value of b can be any integer from 1 to 5. In one embodiment, if more than one B group is present (i.e., b>1), that all such B groups are adjacent to each other. By "adjacent" in this context is meant that no B group has only A groups, as defined below, and/or no substituent groups at all the nearest neighboring points of addition. In the case of an octahedral addition pattern when b>1, "adjacent" means that the four vertices of the octahedron in closest proximity to the B group are not all A groups or null.

In one embodiment, B comprises 18 polar headgroup moieties and b=1.

The polar headgroup moieties of B tend to make the B group or groups hydrophilic.

Each B is bonded to $C_n$ through a covalent bond or bonds. Any covalent bond which a fullerene carbon is capable of forming and will not disrupt the fullerene structure is contemplated. Examples include carbon-carbon, carbon-oxygen, or carbon-nitrogen bonds. One or more atoms, such as one or two atoms, of the B group can participate in bonding to $C_n$. In one embodiment, one carbon atom of the B group is bonded to two carbon atoms of $C_n$, wherein the two carbon atoms of $C_n$ are bonded to each other.

In one embodiment, B has the amide dendron structure

>C(C(=O)OC$_3$H$_6$C(=O)NHC(C$_2$H$_4$C(=O)NHC(C$_2$H$_4$C(=O)OH)$_3$)$_3$)$_2$.

In the amphiphilic fullerene, A is an organic moiety comprising a terminus proximal to the $C_n$ and one or more termini distal to the $C_n$. In one embodiment, the organic moiety comprises two termini distal to $C_n$. By "terminus proximal to $C_n$" is meant a portion of the A group that comprises one or more atoms, such as one or two atoms, of the A group which form a bond or bonds to $C_n$. By "terminus distal to $C_n$" is meant a portion of the A group that does not comprise any atoms which form a bond or bonds to $C_n$, but that does comprise one or more atoms which form a bond or bonds to the terminus of the A group proximal to $C_n$.

Each terminus distal to the $C_n$ comprises —$C_xH_y$, wherein x is an integer and $8 \leq x \leq 24$, and y is an integer and $1 \leq y \leq 2x+1$. The —$C_xH_y$ can be linear, branched, cyclic, aromatic, or some combination thereof. Preferably, A comprises two termini distal to $C_n$, wherein each —$C_xH_y$ is linear, $12 \leq x \leq 18$, and y=2x+1. More preferably, in each of the two termini, x=12 and y=25.

The termini distal to $C_n$ tend to make the A groups hydrophobic or lipophilic.

The value of a can be any integer from 1 to 5. Preferably, a is 5. In one embodiment, if more than one A group is present (i.e., a>1), all such A groups are adjacent to each other. By "adjacent" in this context is meant that no A group has only B groups, as defined below, and/or no substituent groups at all the nearest neighboring points of addition. In the case of an octahedral addition pattern, when a>1, "adjacent" means that the four vertices of the octahedron in closest proximity to the A group are not all B groups or null.

Each A is bonded to $C_n$ through a covalent bond or bonds. Any covalent bond which a fullerene carbon is capable of forming and will not disrupt the fullerene structure is contemplated. Examples include carbon-carbon, carbon-oxygen, or carbon-nitrogen bonds. One or more atoms, such as one or two atoms, of the A group can participate in bonding to $C_n$. In one embodiment, one carbon atom of the A group is bonded to two carbon atoms of $C_n$, wherein the two carbon atoms of $C_n$ are bonded to each other.

In one embodiment, A has the structure >C(C(=O)O(CH$_2$)$_{11}$CH$_3$)$_2$.

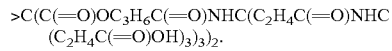

The number of B and A groups is chosen to be from 2 to 6, i.e., $2 \leq b+a \leq 6$. In one embodiment, b+a=6. The combination of hydrophilic B group(s) and hydrophobic A group(s) renders the fullerene amphiphilic. The number and identity of B groups and A groups can be chosen to produce a fullerene with particular amphiphilic qualities which may be desirable for particular intended uses.

The amphiphilic fullerenes are capable of forming a vesicle, wherein the vesicle wall comprises the amphiphilic fullerene. A "vesicle," as the term is used herein, is a collection of amphiphilic molecules, by which is meant, molecules which include both (a) hydrophilic ("water-loving") regions, typically charged or polar moieties, such as moieties comprising polar headgroups, among others known to one of ordinary skill in the art, and (b) hydrophobic ("water-hating") regions, typically apolar moieties, such as hydrocarbon chains, among others known to one of ordinary skill in the art. In aqueous solution, the vesicle is formed when the amphiphilic molecules form a wall, i.e., a closed three-dimensional surface. The wall defines an interior of the vesicle and an exterior of the vesicle. Typically, the exterior surface of the wall is formed by amphiphilic molecules oriented such that their hydrophilic regions are in contact with water, the solvent in the aqueous solution. The interior surface of the wall may be formed by amphiphilic molecules oriented such that their hydrophilic regions are in contact with water present in the interior of the vesicle, or the interior surface of the wall may be formed by amphiphilic molecules oriented such that their hydrophobic regions are in contact with hydrophobic materials present in the interior of the vesicle.

The amphiphilic molecules in the wall will tend to form layers, and therefore, the wall may comprise one or more layers of amphiphilic molecules. If the wall consists of one layer, it may be referred to as a "unilayer membrane" or "monolayer membrane." If the wall consists of two layers, it may be referred to as a "bilayer membrane." Walls with more than two layers, up to any number of layers, are also within the scope of the present invention.

The vesicle may be referred to herein as a "buckysome."

In one embodiment, the vesicle wall is a bilayer membrane. The bilayer membrane comprises two layers, an interior layer formed from the amphiphilic fullerene and other amphiphilic compound or compounds, if any, wherein substantially all the amphiphilic fullerene and other amphiphilic molecules are oriented with their hydrophobic portions toward the exterior layer, and an exterior layer formed from the amphiphilic fullerene and other amphiphilic compound or compounds, if any, wherein substantially all the amphiphilic fullerene and other amphiphilic molecules are oriented with their hydrophobic portions toward the interior layer. As a result, the hydrophilic portions of substantially all molecules of each of the interior and exterior layers are oriented towards aqueous solvent in the vesicle interior or exterior to the vesicle.

For further details on the amphiphilic fullerenes and vesicles made therefrom, see Hirsch et al., U.S. patent application Ser. No. 10/367,646, filed Feb. 14, 2003, for "Use of Buckysome or Carbon Nanotube for Drug Delivery," which is incorporated herein by reference.

In one embodiment, the present invention relates to a composition, comprising:

a substituted fullerene, and a pharmaceutically-acceptable or comestibly-acceptable carrier.

The substituted fullerene can be as described above.

The carrier can be any material or plurality of materials which can form a composition with the substituted fullerene. The particular carrier can be selected by the skilled artisan in view of the intended use of the composition and the properties of the substituted fullerene, among other parameters apparent in light of the present disclosure.

Non-limiting examples of particular carriers and particular compositions follow.

In one embodiment, the carrier is water, and the composition is an aqueous solution comprising water and the substituted fullerene. The composition can further comprise solutes, such as salts, acids, bases, or mixtures thereof, among others. The composition can also comprise a surfactant, an emulsifier, or another compound capable of improving the solubility of the substituted fullerene in water.

In one embodiment, the carrier is a polar organic solvent, and the composition is a polar organic solution comprising the polar organic solvent and the substituted fullerene. "Polar" has its standard meaning in the chemical arts of describing a molecule that has a permanent electric dipole. A polar molecule can but need not have one or more positive, negative, or both charges. Examples of polar organic solvents include, but are not limited to, methanol, ethanol, formate, acrylate, or mixtures thereof, among others. The composition can further comprise solutes, such as salts, among others. The composition can also comprise a surfactant, an emulsifier, or another compound capable of improving the solubility of the substituted fullerene in the polar organic solvent.

In one embodiment, the carrier is an apolar organic solvent, and the composition is an apolar organic solution comprising the apolar organic solvent and the substituted fullerene. "Apolar" has its standard meaning in the chemical arts of describing a molecule that does not have a permanent electric dipole. Examples of apolar organic solvents include, but are not limited to, hexane, cyclohexane, octane, toluene, benzene, or mixtures thereof, among others. The composition can further comprise solutes, such as apolar molecules, among others. The composition can also comprise a surfactant, an emulsifier, or another compound capable of improving the solubility of the substituted fullerene in the apolar organic solvent. In one embodiment, the composition is a water-in-oil emulsion, wherein the substituted fullerene is dissolved in water and water is emulsified into a continuous phase comprising one or more apolar organic solvents.

In one embodiment, the carrier is a mixture of water and other solvents. In one embodiment, the carrier can comprise one or more of dimethicone, water, urea, mineral oil, sodium lactate, polyglyceryl-3 diisostearate, ceresin, glycerin, octyldodecanol, polyglyceryl-2 dipolyhydroxystearate, isopropyl stearate, panthenol, magnesium sulfate, bisabolol, lactic acid, lanolin alcohol, or benzyl alcohol, among others.

In one embodiment, the composition has a creamy consistency suitable for packaging in a squeezable plastic container. In one embodiment, the composition has a lotion consistency suitable for packaging in a squeezable plastic container. In one embodiment, the composition has an ointment-like consistency suitable for packaging in a squeezable plastic container. In one embodiment, the composition has a liquid consistency suitable for packaging in a non-squeezable container. A non-squeezable container can be fabricated from one or more of plastic, glass, metal, ceramic, or other compounds. A non-squeezable container can be fabricated with a flow-type cap or a pump-type dispenser.

In one embodiment, the carrier is a solid or semisolid carrier, and the composition is a solid or semisolid matrix in or over which the substituted fullerene is dispersed. Examples of components of solid carriers include, but are not limited to, sucrose, gelatin, gum arabic, lactose, methylcellulose, cellulose, starch, magnesium stearate, talc, petroleum jelly, or mixtures thereof, among others. The dispersal of the substituted fullerene can be homogeneous (i.e., the distribution of the substituted fullerene can be invariant across all regions of the composition) or heterogeneous (i.e., the distribution of the substituted fullerene can vary at different regions of the composition). The composition can further comprise other materials, such as flavorants, preservatives, or stabilizers, among others.

In one embodiment, the carrier is a gas, and the composition can be a gaseous suspension of the substituted fullerene in the gas, either at ambient pressure or non-ambient pressure. Examples of the gas include, but are not limited to, air, oxygen, nitrogen, or mixtures thereof, among others.

Other carriers will be apparent to the skilled artisan having the benefit of the present disclosure.

In one embodiment, the carrier is a pharmaceutically-acceptable carrier. By "pharmaceutically-acceptable" is meant that the carrier is suitable for use in medicaments intended for administration to a mammal. Parameters which may considered to determine the pharmaceutical acceptability of a carrier can include, but are not limited to, the toxicity of the carrier, the interaction between the substituted fullerene and the carrier, the approval by a regulatory body of the carrier for use in medicaments, or two or more of the foregoing, among others. An example of pharmaceutically-acceptable carrier is an aqueous saline solution. In one embodiment, further components of the composition are pharmaceutically acceptable.

In one embodiment, the carrier is a comestibly-acceptable carrier. By "comestibly-acceptable" is meant that the carrier is suitable for use in food or food packaging wherein the food is intended for feeding to a mammal. Parameters which may considered to determine the comestible acceptability of a carrier can include, but are not limited to, the toxicity of the carrier, the interaction between the substituted fullerene and the carrier, the approval by a regulatory body of the carrier for use in food or food packaging, or two or more of the foregoing, among others. An example of a comestibly-acceptable carrier is starch. In one embodiment, further components of the composition are comestibly acceptable.

In addition to the substituted fullerene and the carrier, and further components described above, the composition can also further comprise other compounds, such as preservatives, adjuvants, excipients, binders, other agents capable of ameliorating one or more diseases, or mixtures thereof, among others. In one embodiment, the other compounds are pharmaceutically acceptable or comestibly acceptable.

The concentration of the substituted fullerene in the composition can vary, depending on the carrier and other parameters apparent to the skilled artisan having the benefit of the present disclosure. The concentration of other components of the composition can also vary along the same lines.

In one embodiment, the present invention relates to a method of ameliorating an oxidative stress disease, comprising:

administering to a mammal an effective amount of a composition comprising a substituted fullerene and a pharmaceutically-acceptable carrier. An "effective amount" of the substituted fullerene is an amount sufficient to ameliorate a disease.

By "ameliorating" a disease is meant improving the condition of a subject suffering or at risk of suffering from the disease. Ameliorating can comprise one or more of the following: a reduction in the severity of a symptom of the disease, a reduction in the extent of a symptom of the disease, a reduction in the number of symptoms of the disease, a reduction in the number of disease agents, a reduction in the spread of a symptom of the disease, a delay in the onset of a symptom of the disease, a delay in disease onset, or a reduction in the time between onset of the disease and remission of the disease, among others apparent to the skilled artisan having the benefit of the present disclosure. To the extent that the foregoing examples of ameliorating a disease are defined in relative terms, the proper comparison is to the disease or symptoms thereof when no composition is administered to ameliorate it and no method is performed to ameliorate it. The terms "preventing" (herein meaning "to stop a disease from onsetting") and "treating" (herein meaning "to improve the condition of a mammal suffering from a disease") are both within the scope of "ameliorating," as used herein.

In the present invention, the disease is an oxidative stress disease. An "oxidative stress disease" is a disease in which the healthy function of one or more organelles, non-organelle subcellular structures, cells, cell types, tissues, tissue types, organs, or organ systems is impaired by the action of oxidizing agents, such as free radicals, particularly radical oxygen species (ROS). The action of oxidizing agents need not be the only route by which impairment of healthy function occurs in the course of a disease for the disease to be an oxidative stress disease. In oxidative stress diseases, a number of sources of oxidizing agents are known. Exemplary sources include, but are not limited to, by-processes of metabolism, irritation by chemicals in the environment (for example, tobacco smoke), or internal challenge (for example, ischemia), among others.

Any one or more of a large number of oxidative stress diseases can be ameliorated by performance of the method.

In one embodiment, the oxidative stress disease is a central nervous system (CNS) neurodegenerative disease. Exemplary CNS neurodegenerative diseases include, but are not limited to, Parkinson's disease, Alzheimer's disease, multiple sclerosis, amyotrophic lateral sclerosis, or Huntington's disease.

In various embodiments, the oxidative stress disease is stroke, atherosclerosis, myocardial ischemia, myocardial reperfusion, or diabetes.

In one embodiment, the oxidative stress disease is a complication of diabetes. Examples of complications of diabetes include, but are not limited to, heart attack, stroke, circulatory impairment, retinopathy, blindness, kidney disease, pancreas disease, neuropathy, gum disease, and skin conditions, among others.

In various embodiments, the oxidative stress disease is circulatory impairment, retinopathy, blindness, kidney disease, pancreas disease, neuropathy, gum disease, cataracts, or skin disease.

In one embodiment, the oxidative stress disease is skin damage. Exemplary causes of skin damage include, but are not limited to, flame, heat, and radiation, such as ultraviolet light (UV), among others.

In one embodiment, the oxidative stress disease is radiation damage, by which is meant damage caused by exposure to alpha particles, beta particles, or electromagnetic radiation, such as UV or gamma rays, among others.

In various embodiments, the oxidative stress disease is damage caused by tobacco use, excessive angiogenesis, or insufficient angiogenesis.

In one embodiment, the oxidative stress disease is senescence. "Senescence," as used herein, refers to one or more of a decrease in the overall health of a mammal, a decrease in the overall fitness of a mammal, or a decrease in the overall quality of life of a mammal, wherein such decrease is generally attributed to the aging process. In one embodiment, ameliorating senescence may lead to maintenance of a particular level of systemic well-being to a later point in the mammal's life. In one embodiment, ameliorating senescence may lead to at least a partial increase in the expected lifespan of the mammal.

Methods of enhancing the overall health and longevity of humans and their companions has been a very active area of research. Given the conserved nature of cellular or developmental processes across metazoans, a number of model organisms have been employed to study senescence, including a nematode, *Caenorhabditis elegans*, and a fruit fly, *Drosophila melanogaster*.

For example, the genetic analysis of *C. elegans* has revealed several genes involved in lifespan determination. Mutations in Daf-2 (an insulin receptor) and Clk-1 ("Clock 1", a gene affecting many aspects of developmental and behavioral timing) have been shown to extend the lifespan of *C. elegans* adults. However, Clk-1 mutants have a higher mortality rate in early life. The Clk-1 longevity phenotype is abolished by mutations in the gene encoding catalase, which is involved in superoxide/free radical metabolism. Additionally, elimination of coenzyme Q in *C. elegans* diet has been shown to extend lifespan. These observations suggest reactive oxygen species are involved in senescence in *C. elegans*.

In *Drosophila*, superoxide dismutase (SOD) and catalase overexpression increased the lifespan by 35%. Mutations in the Methuselah gene ("Mth") have been shown to increase lifespan by 20%. The function of Mth, a G-protein coupled receptor, is not known, but mutants have shown an increased resistance to paraquat (a superoxide radical injury inducing agent). These observations suggest reactive oxygen species are involved in senescence in *Drosophila*.

Dugan et al., Publ. Patent Appl. US 2003/0162837, reported the oral administration of C3 to mice (at about 0.5 mg/kg/day) led to about a 20% increase in mean survival relative to controls (28.7+/−3.3 months vs. 23.5+/−5.5 months, p=0.033).

Hearing loss refers to a state wherein the minimum audible threshold (in dB) of a sound of a particular frequency to a mammal is increased relative to an initial state.

Collateral damage of chemotherapy refers to injuries suffered by healthy tissues of a mammal upon exposure to cytotoxic drugs. Generally, chemotherapy is used in treating certain cancers, but this is not a limitation of the present invention.

Mucositis refers to a fungal infection of a mucous membrane. Fungal infections of mucous membranes are most common among immunocompromised individuals, such as people suffering from HIV infection or certain cancers or undergoing immunosuppressant therapy to combat rejection of transplanted organs, among others. However, fungal infections of the mucous membranes of any mammal are within the scope of "mucositis," as the term is used herein.

In any of the foregoing, the oxidative stress disease inflicts one or more of cell death, cell injury, impaired cell function, the production of cellular products reflective of cell injury, the proliferation of cell types not normally present in a tissue or not normally present in a tissue at such high levels, the degradation or alteration of extracellular matrix, or other symptoms generally recognizable by the skilled artisan as indicating an oxidative stress disease, on the mammal.

The composition and the substituted fullerene and the pharmaceutically-acceptable carrier comprised therein, can be as described above.

The compositions can be made up in any conventional form known in the art of pharmaceutical compounding. Exemplary forms include, but are not limited to, a solid form for oral administration such as tablets, capsules, pills, powders, granules, and the like. In one embodiment, for oral dosage, the composition is in the form of a tablet or a capsule of hard or soft gelatin, methylcellulose, or another suitable material easily dissolved in the digestive tract.

Typical preparations for intravenous administration would be sterile aqueous solutions including water/buffered solutions. Intravenous vehicles include fluid, nutrient and electrolyte replenishers. Preservatives and other additives may also be present.

In the administering step, the composition can be introduced into the mammal by any appropriate technique. An appropriate technique can vary based on the mammal, the oxidative stress disease, and the components of the composition, among other parameters apparent to the skilled artisan having the benefit of the present disclosure. Administration can be systemic, that is, the composition is not directly delivered to a tissue, tissue type, organ, or organ system the function of which is impaired by an oxidative stress disease, or it can be localized, that is, the composition is directly delivered to a tissue, tissue type, organ, or organ system the function of which is impaired by an oxidative stress disease. The route of administration can be varied, depending on the composition and the disease, among other parameters, as a matter of routine experimentation by the skilled artisan having the benefit of the present disclosure. Exemplary routes of administration include transdermal, subcutaneous, intravenous, intraarterial, intramuscular, intrathecal, intraperitoneal, oral, rectal, and nasal, among others. In one embodiment, the route of administration is oral or intravenous.

Fullerenes generally have toxicological properties similar to those of carbon, and substituted fullerenes are generally not expected to possess toxic activities. For example, see Nelson et al., *Toxicology & Indus. Health* (1993) 9(4): 623–630); or Zakharenko et al., *Doklady Akademii Nauk.* (1994) 335(2):261–262.

Though not to be bound by theory, it appears the substituted fullerene can ameliorate an oxidative stress disease by a reaction between the fullerene core and the oxidizing agent, resulting in an oxidizing agent product with lower oxidizing potential than the oxidizing agent. "Oxidizing potential" is used herein to refer to the maximum number of oxidizing reactions an agent can perform on biological molecules.

Any mammal which suffers or is susceptible to an oxidative stress disease can receive the administered composition. An exemplary mammal is Homo sapiens, although other mammals possessing economic or esthetic utility (e.g., livestock such as cattle, sheep, or horses; e.g., pets such as dogs and cats) can receive the administered composition.

An effective amount of the substituted fullerene is one sufficient to affect an amelioration of the disease. The effective amount can vary depending on the identity of the substituted fullerene, or the disease, among others. In one embodiment, the effective amount is such that the dosage of the substituted fullerene to the subject is from about 1 µg/kg body weight/day to about 100 g/kg body weight/day. In a further embodiment, the effective amount is such that the dosage of the substituted fullerene to the subject is from about 1 mg/kg body weight/day to about 1 g/kg body weight/day.

Compositions for bolus intravenous administration may contain from about 1 µg/mL to 10 mg/mL (10,000 mg/liter) of the substituted fullerene. Compositions for drip intravenous administration preferably contain from about 50 mg/liter to about 500 mg/liter of the substituted fullerene.

In one embodiment, compositions for oral dosage are in the form of capsules or tablets containing from 50 mg to 500 mg of the substituted fullerene. For ameliorating a chronic disease, the method can be performed one or more times per day for an indefinite period. For ameliorating an acute disease, such as stroke or myocardial ischemia, among others, the method can be performed one or more times for a brief period following the onset of the acute insult. Alternative durations of method performance are a matter of routine experimentation for the skilled artisan having the benefit of the present disclosure.

In one embodiment, the present invention relates to a method of ameliorating damage to tissues for transplantation, ameliorating spoilage of food, inhibiting microbes, or reducing free radical levels in tobacco, comprising:

contacting the tissues for transplantation, the food, the microbes, or the tobacco with an effective amount of a composition comprising a substituted fullerene and a pharmaceutically-acceptable or comestibly-acceptable carrier, as described above. An "effective amount" of the substituted fullerene is an amount sufficient to ameliorate the damage, ameliorate the spoilage, inhibit the microbes, or reduce the free radical levels, as applicable.

By "ameliorating" damage to tissues for transplantation is meant reducing oxidative damage to stored tissues. The stored tissues can be derived from cadavers, from living donors, or from tissues which may be grown, at present or in the future, by in vitro techniques. The stored tissues can be derived from humans or other animals, such as cattle or swine, among others, and can, but need not, be stored against implantation in a human or another animal. Examples of such tissues include, but are not limited to, whole blood, blood fractions, valves from the circulatory system, vessels and vessel portions from the circulatory system, hearts, lungs, corneas, kidneys, and livers, among others.

By "ameliorating" spoilage of food is meant at least one of reducing oxidative damage to stored food or extending the shelf-life of stored food, among others apparent to the skilled artisan having the benefit of the present disclosure.

"Food" refers to any product which both (a) possesses nutritive value to humans or animals having economic, esthetic, or research value to humans and (b) is suitable for oral ingestion into the gastrointestinal tract.

By "inhibiting" microbes is meant at least one of reducing the number of microbes in a substrate susceptible to microbial culture, reducing the rate of growth of a microbe population in such a substrate, reducing the maximum population of a microbe population in such a substrate, or increasing the number of microbes required to establish a microbial culture in such a substrate, among others apparent to the skilled artisan having the benefit of the present disclosure. A "microbe" is any organism, virus, prion, or other biological molecule or collection of biological molecules capable of duplicating themselves or being duplicated under specific in vitro or in vivo conditions suitable for such duplication, wherein the organism or the like has a maximum dimension of 100 microns or less. Examples of microbes include various invertebrates, fungi, bacteria, cyanobacteria, archebacteria, viruses, and prions, among others.

By "reducing" free radical levels in tobacco is meant reducing the overall oxidizing potential of a tobacco composition. A "tobacco composition" is any compound containing nicotine, such as more than about 0.1 wt % nicotine. Typically, but not necessarily, the tobacco composition contains biological product of a plant of genus *Nicotiana*. Exemplary tobacco compositions include, but are not limited to, *Nicotiana* leaf (including fresh, dried, processed, whole, or comminuted leaf, among others), cigarette filler, cigar filler, pipe tobacco, chewing tobacco, snuff, maceration products of any of the foregoing, and combustion products of any of the foregoing, among others.

To the extent that the foregoing examples of ameliorating, inhibiting, or reducing are defined in relative terms, the proper comparison is to the condition obtaining when no composition is administered to the tissues for transplantation, food, microbes, or tobacco composition to ameliorate, etc. and no method is performed to ameliorate, etc.

The composition, and the substituted fullerene and the carrier comprised therein, can be as described above. The carrier can be a pharmaceutically-acceptable carrier or a comestibly-acceptable carrier.

In the contacting step, the tissue for transplantation, food, microbe, or tobacco composition can be contacted with the composition containing the substituted fullerene. The technique for contacting can be varied depending on the item to be contacted and the composition containing the substituted fullerene, among other parameters, as a matter of routine experimentation for the skilled artisan having the benefit of the present disclosure.

In one embodiment, wherein the item to be contacted is a tissue for transplantation and the composition is a liquid, the composition can be poured over or injected into the tissue, or the like.

In one embodiment, wherein the item to be contacted is a solid food and the composition is a solid, the composition can be dispersed in the food or contained in a sachet located in the food or affixed to an interior surface of a container containing the food.

In one embodiment, wherein the item to be contacted is a liquid food and the composition is a solid, the composition can be dissolved or suspended in the food or contained in a sachet located in the food or affixed to an interior surface of a container containing the food.

In one embodiment, wherein the item to be contacted is a liquid food and the composition is a liquid, the composition can be dissolved or mixed in the food or contained in a sachet located in the food or affixed to an interior surface of a container containing the food.

In one embodiment, wherein the item to be contacted is a microbe located on a substrate (such as a surface for which microbial inhibition is desired) and the composition is a liquid, the composition can be sprayed, poured, or the like onto the substrate.

In one embodiment, wherein the item to be contacted is a tobacco composition, and the substituted fullerene composition is a solid, the composition can be mixed into the tobacco composition or impregnated into a cigarette filter. In one embodiment, wherein the item to be contacted is a tobacco composition, and the substituted fullerene composition is a liquid, the composition can be sprayed onto the tobacco composition or into a cigarette filter.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Superoxide radicals were generated by employing the xanthine/xanthine oxidase/cytochrome c system. The reaction was initiated by the addition of xanthine oxidase ($7.5 \times 10^{-3}$ units) to the incubation mixture and the reaction was followed in terms of the reduction of cytochrome c and the corresponding increase in the absorbance at 550 nm. The reduction of ferricytochrome c into ferrocytochrome c was determined using the molar absorption coefficients of 9 $mmol^{-1}$ $cm^{-1}$ and 27.7 $mmol^{-1}$ $cm^{-1}$, for the oxidized and reduced forms, respectively. All assays were performed at room temperature. The incubation mixture consisted of 50 mM potassium phosphate, 0.1 mM EDTA, 0.01 mM cytochrome c, and 0.05 mM xanthine, along with the indicated concentration of antioxidant. A total volume of 0.3 mL was used in each experiment.

Various substituted fullerenes, both those known in the art and those reported herein, were tested, as shown in FIG. 10. Trolox, a known non-fullerene antioxidant, was tested as a comparative example. A negative control (without antioxidant, not shown) was run to establish a baseline for the reduction of cytochrome c. The compounds and their $IC_{50}$ values are given in FIG. 10. Comparative compounds are indicated with the notation "(Comparative)."

Of the comparative compounds, DF-1 had the lowest $IC_{50}$, 102 µM. However, many of the compounds of the present invention had much lower $IC_{50}$ values, indicating higher antioxidant properties.

All of the compositions and the methods disclosed and claimed herein can be made and executed without undue experimentation in light of the present disclosure. While the compositions and methods of this invention have been described in terms of particular embodiments, it will be apparent to those of skill in the art that variations may be applied to the compositions and the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A substituted fullerene, comprising a fullerene core (Cn), wherein n is an even integer greater than or equal to 60, and at least one of i–iv:
   (i) m (>CX$^1$X$^2$) groups bonded to the fullerene core, wherein:
      (i-a) m is an integer from 1 to 6, inclusive,
      (i-b) each X$^1$ and X$^2$ is independently selected from —H; —COOH; —CONH$_2$; —CONHR'; —CONR'$_2$; —COOR'; —CHO; —(CH$_2$)$_d$OH; a peptidyl moiety; —R; —RCOOH; —RCONH$_2$; —RCONHR'; —RCONR'$_2$; —RCOOR'; —RCHO; —R(CH$_2$)$_d$OH; a heterocyclic moiety; a branched moiety comprising one or more terminal —OH, —NH$_2$, triazole, tetrazole, or sugar groups; or a salt thereof, wherein each R is a hydrocarbon moiety having from 1 to about 6 carbon atoms and each R' is independently a hydrocarbon moiety having from 1 to about 6 carbon atoms, an aryl-containing moiety having from 6 to about 18 carbon atoms, a hydrocarbon moiety having from 1 to about 6 carbon atoms and a terminal carboxylic acid or alcohol, or an aryl-containing moiety having from 6 to about 18 carbon atoms and a terminal carboxylic acid or alcohol, and d is an integer from 0 to about 20; and
      (i-c) when m is 3, at least one X$^1$ or X$^2$ is not —COOH;
   (ii) p —X$^3$ groups bonded to the fullerene core, wherein:
      (ii-a) p is an integer from 1 to 18, inclusive; and
      (ii-b) each —X$^3$ is independently selected from —N$^+$(R$^2$)(R$^3$)(R$^4$), wherein R$^2$, R$^3$, and R$^4$ are independently —H or —(CH$_2$)$_d$—CH$_3$, wherein d is an integer from 0 to about 20; —N$^+$(R$^2$)(R$^3$)(R$^8$), wherein R$^2$ and R$^3$ are independently —H or —(CH$_2$)$_d$—CH$_3$, wherein d is an integer from 0 to about 20, and each R$^8$ is independently —(CH$_2$)$_f$—SO$_3^-$, —(CH$_2$)$_f$—PO$_4^-$, or —(CH$_2$)$_f$—COO$^-$, wherein f is an integer from 1 to about 20; —C(R$^5$)(R$^6$)(R$^7$), wherein R$^5$, R$^6$, and R$^7$ are independently —COOH, —H, —CH(=O), —CH$_2$OH, or a peptidyl moiety; —C(R$^2$)(R$^3$)(R$^8$), wherein R$^2$ and R$^3$ are independently —H or —(CH$_2$)$_d$—CH$_3$, wherein d is an integer from 0 to about 20, and each R$^8$ is independently —(CH$_2$)$_f$—SO$_3^-$, —(CH$_2$)$_f$—PO$_4^-$, or —(CH$_2$)$_f$—COO$^-$, wherein f is an integer from 1 to about 20; —(CH$_2$)$_e$—COOH, —(CH$_2$)$_e$—CONH$_2$, —(CH$_2$)$_e$—COOR', wherein e is an integer from 1 to about 6 and each R' is independently a hydrocarbon moiety having from 1 to about 6 carbon atoms, an aryl-containing moiety having from 6 to about 18 carbon atoms, a hydrocarbon moiety having from 1 to about 6 carbon atoms and a terminal carboxylic acid or alcohol, or an aryl-containing moiety having from 6 to about 18 carbon atoms and a terminal carboxylic acid or alcohol; a peptidyl moiety; or an aromatic heterocyclic moiety containing a cationic nitrogen;
   (iii) q —X$^4$— groups bonded to the fullerene core, wherein
      (iii-a) q is an integer from 1 to 6, inclusive; and
      (iii-b) each —X$^4$— group is independently

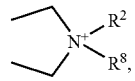

wherein R$^2$ is independently —H or —(CH$_2$)$_d$—CH$_3$, d is an integer from 0 to about 20, and R$^8$ is independently —(CH$_2$)$_f$—SO$_3^-$, —(CH$_2$)$_f$—PO$_4^-$, or —(CH$_2$)$_f$—COO$^-$, and f is an integer from 1 to about 20;

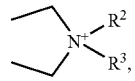

wherein each R$^2$ and R$^3$ is independently —H or —(CH$_2$)$_d$—CH$_3$ and d is an integer from 0 to about 20; or

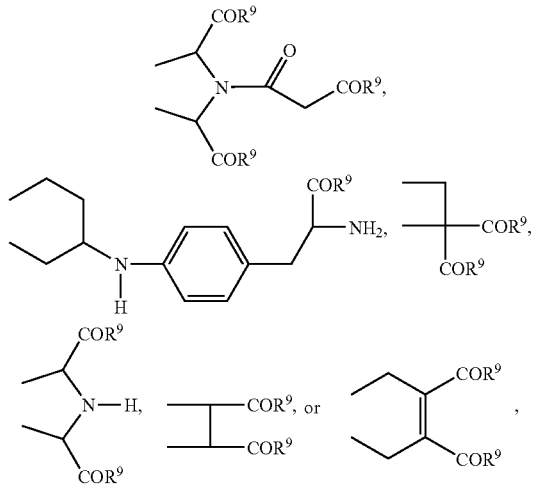

wherein each R$^2$ is independently —H or —(CH$_2$)$_d$—CH$_3$, d is an integer from 0 to about 20, and each R$^9$ is independently —H, —OH, —OR', —NH$_2$, —NHR', —NHR'$_2$, or —(CH$_2$)$_d$OH, wherein each R' is independently a hydrocarbon moiety having from 1 to about 6 carbon atoms, an aryl-containing moiety having from 6 to about 18 carbon atoms, a hydrocarbon moiety having from 1 to about 6 carbon atoms and a terminal carboxylic acid or alcohol, or an aryl-containing moiety having from 6 to about 18 carbon atoms and a terminal carboxylic acid or alcohol.

(iv) r dendrons bonded to the fullerene core and s nondendrons bonded to the fullerene core, wherein:
      (iv-a) r is an integer from 1 to 6, inclusive;
      (iv-b) s is an integer from 0 to 18, inclusive;
      (iv-b) each dendron has at least one protic group which imparts water solubility,
      (iv-d) each nondendron independently comprises at least one drug, amino acid, peptide, nucleotide, vitamin, or organic moiety, and
      (iv-e) when r is 1 and the dendron comprises 18 —COOH groups, s is an integer from 1 to 18, inclusive.

2. The substituted fullerene of claim 1, wherein the substituted fullerene comprises a fullerene core (Cn) having 60 carbon atoms or 70 carbon atoms.

3. The substituted fullerene of claim 1, wherein the substituted fullerene comprises $C_{60}$ and 3 (>$CX^1X^2$) groups in the C3 orientation or the D3 orientation.

4. The substituted fullerene of claim 1, wherein the substituted fullerene comprises $C_{60}$ and 2 (>$CX^1X^2$) groups in the trans-2 orientation, the trans-3 orientation, the e orientation, or the cis-2 orientation.

5. The substituted fullerene of claim 1, wherein the substituted fullerene comprises $C_{70}$ and 2 (>$CX^1X^2$) groups in the bis orientation.

6. The substituted fullerene of claim 1, wherein n is 60, m is 3, p is 0, q is 0, r is 0, s is 0, from 1 to 3 $X^1$, inclusive, are —H, and all $X^2$ are —COOH.

7. The substituted fullerene of claim 1, wherein the substituted fullerene has the structure shown in FIG. 7B.

8. The substituted fullerene of claim 1, wherein the substituted fullerene has a structure selected from FIGS. 8A–8G.

9. The substituted fullerene of claim 1, wherein m is 3, p is 0, q is 0, r is 0, s is 0, and at least one $X^1$ is a peptidyl moiety selected from —C(=O)O—(CH$_2$)$_3$—C(=O)-alanine, —C(=O)O—(CH$_2$)$_3$—C(=O)-alanine-phenylalanine, or —C(=O)O—(CH$_2$)$_3$—C(=O)-alanine-alanine.

10. The substituted fullerene of claim 1, wherein m is 3, p is 0, q is 0, r is 0, s is 0, and at least one $X^1$ is a peptidyl moiety selected from Z-D-Phe-L-Phe-Gly, Z-L-Phe, Z-Gly-L-Phe-L-Phe, Z-Gly-L-Phe, Z-L-Phe-L-Phe, Z-L-Phe-L-Tyr, Z-L-Phe-Gly, Z-L-Phe-L-Met, Z-L-Phe-L-Ser, Z-Gly-L-Phe-L-Phe-Gly, wherein Z is a carbobenzoxy group.

11. The substituted fullerene of claim 1, wherein the substituted fullerene comprises an endohedral metal.

12. A composition, comprising:
a carrier, and,
a substituted fullerene, comprising a fullerene core (Cn), wherein n is an even integer greater than or equal to 60, and at least one of i-iv:
(i) m (>$CX^1X^2$) groups bonded to the fullerene core, wherein:
(i-a) m is an integer from 1 to 6, inclusive,
(i-b) each $X^1$ and $X^2$ is independently selected from —H; —COOH; —CONH$_2$; —CONHR'; —CONR'$_2$; —COOR'; —CHO; —(CH$_2$)$_d$OH; a peptidyl moiety; —R; —RCOOH; —RCONH$_2$; —RCONHR'; —RCONR'$_2$; —RCOOR'; —RCHO; —R(CH$_2$)$_d$OH; a heterocyclic moiety; a branched moiety comprising one or more terminal —OH, —NH$_2$, triazole, tetrazole, or sugar groups; or a salt thereof, wherein each R is a hydrocarbon moiety having from 1 to about 6 carbon atoms and each R' is independently a hydrocarbon moiety having from 1 to about 6 carbon atoms, an aryl-containing moiety having from 6 to about 18 carbon atoms, a hydrocarbon moiety having from 1 to about 6 carbon atoms and a terminal carboxylic acid or alcohol, or an aryl-containing moiety having from 6 to about 18 carbon atoms and a terminal carboxylic acid or alcohol, and d is an integer from 0 to about 20; and
(i-c) when m is 3, at least one $X^1$ or $X^2$ is not —COOH;
(ii) p —$X^3$ groups bonded to the fullerene core, wherein:
(ii-a) p is an integer from 1 to 18, inclusive; and
(ii-b) each —$X^3$ is independently selected from —N$^+$(R$^2$)(R$^3$)(R$^4$), wherein R$^2$, R$^3$, and R$^4$ are independently —H or —(CH$_2$)$_d$—CH$_3$, wherein d is an integer from 0 to about 20; —N$^+$(R$^2$)(R$^3$)(R$^8$), wherein R$^2$ and R$^3$ are independently —H or —(CH$_2$)$_d$—CH$_3$, wherein d is an integer from 0 to about 20, and each R$^8$ is independently —(CH$_2$)$_f$—SO$_3^-$, —(CH$_2$)$_f$—PO$_4^-$, or —(CH$_2$)$_f$—COO$^-$, wherein f is an integer from 1 to about 20; —C(R$^5$)(R$^6$)(R$^7$), wherein R$^5$, R$^6$, and R$^7$ are independently —COOH, —H, —CH(=O), —CH$_2$OH, or a peptidyl moiety; —C(R$^2$)(R$^3$)(R$^8$), wherein R$^2$ and R$^3$ are independently —H or —(CH$_2$)$_d$—CH$_3$, wherein d is an integer from 0 to about 20, and each R$^8$ is independently —(CH$_2$)$_f$—SO$_3^-$, —(CH$_2$)$_f$—PO$_4^-$, or —(CH$_2$)$_f$—COO$^-$, wherein f is an integer from 1 to about 20; —(CH$_2$)$_e$—COOH, —(CH$_2$)$_e$—CONH$_2$, —(CH$_2$)$_e$—COOR', wherein e is an integer from 1 to about 6 and each R' is independently a hydrocarbon moiety having from 1 to about 6 carbon atoms, an aryl-containing moiety having from 6 to about 18 carbon atoms, a hydrocarbon moiety having from 1 to about 6 carbon atoms and a terminal carboxylic acid or alcohol, or an aryl-containing moiety having from 6 to about 18 carbon atoms and a terminal carboxylic acid or alcohol; a peptidyl moiety; or an aromatic heterocyclic moiety containing a cationic nitrogen;

(iii) q —$X^4$— groups bonded to the fullerene core, wherein
(iii-a) q is an integer from 1 to 6, inclusive; and
(iii-b) each —$X^4$— group is independently

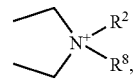

wherein R$^2$ is independently —H or —(CH$_2$)$_d$—CH$_3$, d is an integer from 0 to about 20, and R$^8$ is independently —(CH$_2$)$_f$—SO$_3^-$, —(CH$_2$)$_f$—PO$_4^-$, or —(CH$_2$)$_f$—COO$^-$, and f is an integer from 1 to about 20;

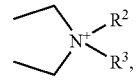

wherein each R$^2$ and R$^3$ is independently —H or —(CH$_2$)$_d$—CH$_3$ and d is an integer from 0 to about 20; or

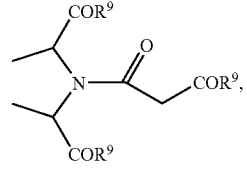

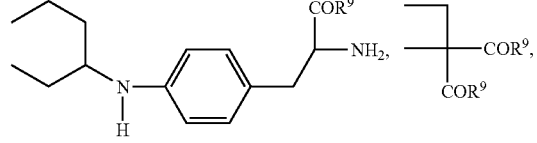

-continued

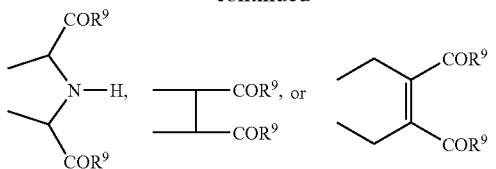

wherein each R² is independently —H or —(CH₂)_d—CH₃, d is an integer from 0 to about 20, and each R⁹ is independently —H, —OH, —OR', —NH₂, —NHR', —NHR'₂, or —(CH₂)_dOH, wherein each R' is independently a hydrocarbon moiety having from 1 to about 6 carbon atoms, an aryl-containing moiety having from 6 to about 18 carbon atoms, a hydrocarbon moiety having from 1 to about 6 carbon atoms and a terminal carboxylic acid or alcohol, or an aryl-containing moiety having from 6 to about 18 carbon atoms and a terminal carboxylic acid or alcohol.

(iv) r dendrons bonded to the fullerene core and s non-dendrons bonded to the fullerene core, wherein:
(iv-a) r is an integer from 1 to 6, inclusive;
(iv-b) s is an integer from 0 to 18, inclusive;
(iv-b) each dendron has at least one protic group which imparts water solubility,
(iv-d) each nondendron independently comprises at least one drug, amino acid, peptide, nucleotide, vitamin, or organic moiety, and
(iv-e) when r is 1 and the dendron comprises 18 —COOH groups, s is an integer from 1 to 18, inclusive.

13. The composition of claim 12, wherein the carrier is a pharmaceutically-acceptable carrier or a comestibly-acceptible carrier.

14. The composition of claim 12, wherein the substituted fullerene comprises a fullerene core (Cn) having 60 carbon atoms or 70 carbon atoms.

15. The composition of claim 12, wherein the substituted fullerene comprises C₆₀ and 3 (>CX¹X²) groups in the C3 orientation or the D3 orientation.

16. The composition of claim 12, wherein the substituted fullerene comprises C₆₀ and 2 (>CX¹X²) groups in the trans-2 orientation, the trans-3 orientation, the e orientation, or the cis-2 orientation.

17. The composition of claim 12, wherein the substituted fullerene comprises C₇₀ and 2 (>CX¹X²) groups in the bis orientation.

18. The composition of claim 12, wherein n is 60, m is 3, p is 0, q is 0, r is 0, s is 0, from 1 to 3 X¹, inclusive, are —H, and all X² are —COOH.

19. The composition of claim 12, wherein the substituted fullerene has the structure shown in FIG. 7B.

20. The composition of claim 12, wherein the substituted fullerene has a structure selected from FIGS. 8A–8G.

21. The composition of claim 12, wherein m is 3, p is 0, q is 0, r is 0, s is 0, and at least one X¹ is a peptidyl moiety selected from —C(=O)O—(CH₂)₃—C(=O)-alanine, —C(=O)O—(CH₂)₃—C(=O)-alanine-phenylalanine, or —C(=O)O—(CH₂)₃—C(=O)-alanine-alanine.

22. The composition of claim 12, wherein m is 3, p is 0, q is 0, r is 0, s is 0, and at least one X¹ is a peptidyl moiety selected from Z-D-Phe-L-Phe-Gly, Z-L-Phe, Z-Gly-L-Phe-L-Phe, Z-Gly-L-Phe, Z-L-Phe-L-Phe, Z-L-Phe-L-Tyr, Z-L-Phe-Gly, Z-L-Phe-L-Met, Z-L-Phe-L-Ser, Z-Gly-L-Phe-L-Phe-Gly, wherein Z is a carbobenzoxy group.

23. The composition of claim 12, wherein the substituted fullerene comprises an endohedral metal.

24. A method of ameliorating an oxidative stress disease, comprising:
administering to a mammal an effective amount of a composition comprising a substituted fullerene, wherein the substituted fullerene comprises a fullerene core (Cn), wherein n is an even integer greater than or equal to 60, and at least one of i-iv:

(i) m (>CX¹X²) groups bonded to the fullerene core, wherein:
(i-a) m is an integer from 1 to 6, inclusive,
(i-b) each X¹ and X² is independently selected from —H; —COOH; —CONH₂; —CONHR'; —CONR'₂; —COOR'; —CHO; —(CH₂)_dOH; a peptidyl moiety; —R; —RCOOH; —RCONH₂; —RCONHR'; —RCONR'₂; —RCOOR'; —RCHO; —R(CH₂)_dOH; a heterocyclic moiety; a branched moiety comprising one or more terminal —OH, —NH₂, triazole, tetrazole, or sugar groups; or a salt thereof, wherein each R is a hydrocarbon moiety having from 1 to about 6 carbon atoms and each R' is independently a hydrocarbon moiety having from 1 to about 6 carbon atoms, an aryl-containing moiety having from 6 to about 18 carbon atoms, a hydrocarbon moiety having from 1 to about 6 carbon atoms and a terminal carboxylic acid or alcohol, or an aryl-containing moiety having from 6 to about 18 carbon atoms and a terminal carboxylic acid or alcohol, and d is an integer from 0 to about 20; and
(i-c) when m is 3, at least one X¹ or X² is not —COOH;

(ii) p —X³ groups bonded to the fullerene core, wherein:
(ii-a) p is an integer from 1 to 18, inclusive; and
(ii-b) each —X³ is independently selected from —N⁺(R²)(R³)(R⁴), wherein R², R³, and R⁴ are independently —H or —(CH₂)_d—CH₃, wherein d is an integer from 0 to about 20; —N⁺(R²)(R³)(R⁸), wherein R² and R³ are independently —H or —(CH₂)_d—CH₃, wherein d is an integer from 0 to about 20, and each R⁸ is independently —(CH₂)_f—SO₃⁻, —(CH₂)_f—PO₄⁻, or —(CH₂)_f—COO⁻, wherein f is an integer from 1 to about 20; —C(R⁵)(R⁶)(R⁷), wherein R⁵, R⁶, and R⁷ are independently —COOH, —H, —CH(=O), —CH₂OH, or a peptidyl moiety; —C(R²)(R³)(R⁸), wherein R² and R³ are independently —H or —(CH₂)_d—CH₃, wherein d is an integer from 0 to about 20, and each R⁸ is independently —(CH₂)_f—SO₃⁻, —(CH₂)_f—PO₄⁻, or —(CH₂)_f—COO⁻, wherein f is an integer from 1 to about 20; —(CH₂)_e—COOH, —(CH₂)_e—CONH₂, —(CH₂)_e—COOR', wherein e is an integer from 1 to about 6 and each R' is independently a hydrocarbon moiety having from 1 to about 6 carbon atoms, an aryl-containing moiety having from 6 to about 18 carbon atoms, a hydrocarbon moiety having from 1 to about 6 carbon atoms and a terminal carboxylic acid or alcohol, or an aryl-containing moiety having from 6 to about 18 carbon atoms and a terminal carboxylic acid or alcohol; a peptidyl moiety; or an aromatic heterocyclic moiety containing a cationic nitrogen;

(iii) q —X⁴— groups bonded to the fullerene core, wherein
(iii-a) q is an integer from 1 to 6, inclusive; and
(iii-b) each —X⁴— group is independently

wherein $R^2$ is independently —H or —$(CH_2)_d$—$CH_3$, d is an integer from 0 to about 20, and $R^8$ is independently —$(CH_2)_f$—$SO_3^-$, —$(CH_2)_f$—$PO_4^-$, or —$(CH_2)_f$—$COO^-$, and f is an integer from 1 to about 20;

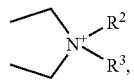

wherein each $R^2$ and $R^3$ is independently —H or —$(CH_2)_d$—$CH_3$ and d is an integer from 0 to about 20; or

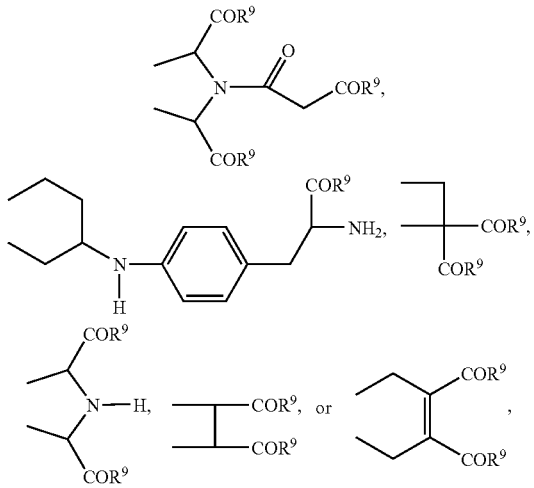

wherein each $R^2$ is independently —H or —$(CH_2)_d$—$CH_3$, d is an integer from 0 to about 20, and each $R^9$ is independently —H, —OH, —OR', —$NH_2$, —NHR', —$NHR'_2$, or —$(CH_2)_d$OH, wherein each R' is independently a hydrocarbon moiety having from 1 to about 6 carbon atoms, an aryl-containing moiety having from 6 to about 18 carbon atoms, a hydrocarbon moiety having from 1 to about 6 carbon atoms and a terminal carboxylic acid or alcohol, or an aryl-containing moiety having from 6 to about 18 carbon atoms and a terminal carboxylic acid or alcohol, (iv) r dendrons bonded to the fullerene core and s nondendrons bonded to the fullerene core, wherein:
(iv-a) r is an integer from 1 to 6, inclusive;
(iv-b) s is an integer from 0 to 18, inclusive;
(iv-b) each dendron has at least one protic group which imparts water solubility,
(iv-d) each nondendron independently comprises at least one drug, amino acid, peptide, nucleotide, vitamin, or organic moiety, and
(iv-e) when r is 1 and the dendron comprises 18 —COOH groups, s is an integer from 1 to 18, inclusive.

25. The method of claim 24, wherein the mammal suffers or is susceptible to an oxidative stress disease selected from central nervous system (CNS) neurodegenerative diseases, stroke, atherosclerosis, myocardial ischemia, myocardial reperfusion, diabetes, complications of diabetes, circulatory impairment, retinopathy, blindness, kidney disease, pancreas disease, neuropathy, gum disease, cataracts, skin disease, skin damage, radiation damage, damage caused by tobacco use, excessive angiogenesis, insufficient angiogenesis, hearing loss, collateral damage of chemotherapy; mucositis, or senescence.

26. The method of claim 25, wherein the CNS neurodegenerative disease is Parkinson's disease, Alzheimer's disease, multiple sclerosis, amyotrophic lateral sclerosis, or Huntington's disease.

27. The method of claim 25, further comprising a pharmaceutically-acceptable carrier or a comestibly-acceptable carrier.

28. The method of claim 25, wherein the substituted fullerene comprises a fullerene core (Cn) having 60 carbon atoms or 70 carbon atoms.

29. The method of claim 25, wherein the substituted fullerene comprises $C_{60}$ and 3 ($>CX^1X^2$) groups in the C3 orientation or the D3 orientation.

30. The method of claim 25, wherein the substituted fullerene comprises $C_{60}$ and 2 ($>CX^1X^2$) groups in the trans-2 orientation, the trans-3 orientation, the e orientation, or the cis-2 orientation.

31. The method of claim 25, wherein the substituted fullerene comprises $C_{70}$ and 2 ($>CX^1X^2$) groups in the bis orientation.

32. The method of claim 25, wherein n is 60, m is 3, p is 0, q is 0, r is 0, s is 0, from 1 to 3 $X^1$, inclusive, are —H, and all $X^2$ are —COOH.

33. The method of claim 25, wherein the substituted fullerene has the structure shown in FIG. 7B.

34. The method of claim 25, wherein the substituted fullerene has a structure selected from FIGS. 8A–8G.

35. The method of claim 25, wherein m is 3, p is 0, q is 0, r is 0, s is 0, and at least one $X^1$ is a peptidyl moiety selected from —C(=O)O—$(CH_2)_3$—C(=O)-alanine, —C(=O)O—$(CH_2)_3$—C(=O)-alanine-phenylalanine, or —C(=O)O—$(CH_2)_3$—C(=O)-alanine-alanine.

36. The method of claim 25, wherein m is 3, p is 0, q is 0, r is 0, s is 0, and at least one $X^1$ is a peptidyl moiety selected from Z-D-Phe-L-Phe-Gly, Z-L-Phe, Z-Gly-L-Phe-L-Phe, Z-Gly-L-Phe, Z-L-Phe-L-Phe, Z-L-Phe-L-Tyr, Z-L-Phe-Gly, Z-L-Phe-L-Met, Z-L-Phe-L-Ser, Z-Gly-L-Phe-L-Phe-Gly, wherein Z is a carbobenzoxy group.

37. The method of claim 25, wherein the substituted fullerene comprises an endohedral metal.

38. A method of ameliorating damage to tissues for transplantation, ameliorating spoilage of food, inhibiting microbes, or reducing free radical levels in tobacco, comprising:
contacting the tissues for transplantation, the food, the microbes, or the tobacco with an effective amount of a composition comprising a substituted fullerene and a carrier, wherein the substituted fullerene comprises a fullerene core (Cn), wherein n is an even integer greater than or equal to 60, and at least one of i-iv:
(i) m ($>CX^1X^2$) groups bonded to the fullerene core, wherein:
(i-a) m is an integer from 1 to 6, inclusive,
(i-b) each $X^1$ and $X^2$ is independently selected from —H; —COOH; —$CONH_2$; —CONHR'; —$CONR'_2$; —COOR'; —CHO; —$(CH_2)_d$OH; a peptidyl moiety;

—R; —RCOOH; —RCONH$_2$; —RCONHR'; —RCONR'$_2$; —RCOOR'; —RCHO; —R(CH$_2$)$_d$OH; a heterocyclic moiety; a branched moiety comprising one or more terminal —OH, —NH$_2$, triazole, tetrazole, or sugar groups; or a salt thereof, wherein each R is a hydrocarbon moiety having from 1 to about 6 carbon atoms and each R' is independently a hydrocarbon moiety having from 1 to about 6 carbon atoms, an aryl-containing moiety having from 6 to about 18 carbon atoms, a hydrocarbon moiety having from 1 to about 6 carbon atoms and a terminal carboxylic acid or alcohol, or an aryl-containing moiety having from 6 to about 18 carbon atoms and a terminal carboxylic acid or alcohol, and d is an integer from 0 to about 20; and (i-c) when m is 3, at least one X$^1$ or X$^2$ is not —COOH;

(ii) p —X$^3$ groups bonded to the fullerene core, wherein:

(ii-a) p is an integer from 1 to 18, inclusive; and (ii-b) each —X$^3$ is independently selected from —N$^+$(R$^2$)(R$^3$)(R$^4$), wherein R$^2$, R$^3$, and R$^4$ are independently —H or —(CH$_2$)$_d$—CH$_3$, wherein d is an integer from 0 to about 20; —N$^+$(R$^2$)(R$^3$)(R$^8$), wherein R$^2$ and R$^3$ are independently —H or —(CH$_2$)$_d$—CH$_3$, wherein d is an integer from 0 to about 20, and each R$^8$ is independently —(CH$_2$)$_f$—SO$_3^-$, —(CH$_2$)$_f$—PO$_4^-$, or —(CH$_2$)$_f$—COO$^-$, wherein f is an integer from 1 to about 20; —C(R$^5$)(R$^6$)(R$^7$), wherein R$^5$, R$^6$, and R$^7$ are independently —COOH, —H, —CH(=O), —CH$_2$OH, or a peptidyl moiety; —C(R$^2$)(R$^3$)(R$^8$), wherein R$^2$ and R$^3$ are independently —H or —(CH$_2$)$_d$—CH$_3$, wherein d is an integer from 0 to about 20, and each R$^8$ is independently —(CH$_2$)$_f$—SO$_3^-$, —(CH$_2$)$_f$—PO$_4^-$, or —(CH$_2$)$_f$—COO$^-$, wherein f is an integer from 1 to about 20; —(CH$_2$)$_e$—COOH, —(CH$_2$)$_e$—CONH$_2$, —(CH$_2$)$_e$—COOR', wherein e is an integer from 1 to about 6 and each R' is independently a hydrocarbon moiety having from 1 to about 6 carbon atoms, an aryl-containing moiety having from 6 to about 18 carbon atoms, a hydrocarbon moiety having from 1 to about 6 carbon atoms and a terminal carboxylic acid or alcohol, or an aryl-containing moiety having from 6 to about 18 carbon atoms and a terminal carboxylic acid or alcohol; a peptidyl moiety; or an aromatic heterocyclic moiety containing a cationic nitrogen;

(iii) q —X$^4$— groups bonded to the fullerene core, wherein (iii-a) q is an integer from 1 to 6, inclusive; and (iii-b) each —X$^4$— group is independently

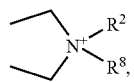

wherein R$^2$ is independently —H or —(CH$_2$)$_d$—CH$_3$, d is an integer from 0 to about 20, and R$^8$ is independently —(CH$_2$)$_f$—SO$_3^-$, —(CH$_2$)$_f$—PO$_4^-$, or —(CH$_2$)$_f$—COO$^-$, and f is an integer from 1 to about 20;

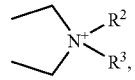

wherein each R$^2$ and R$^3$ is independently —H or —(CH$_2$)$_d$—CH$_3$ and d is an integer from 0 to about 20; or

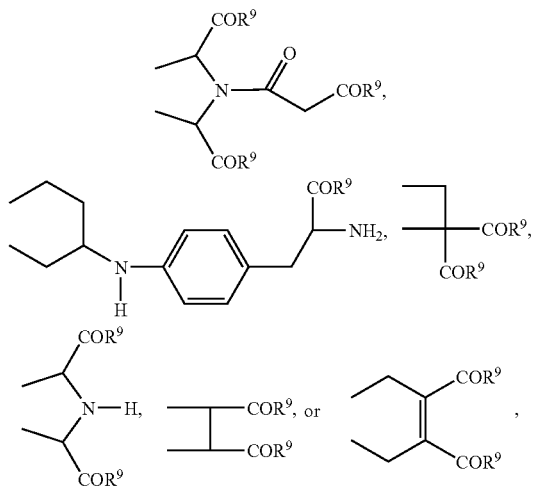

wherein each R$^2$ is independently —H or —(CH$_2$)$_d$—CH$_3$, d is an integer from 0 to about 20, and each R$^9$ is independently —H, —OH, —OR', —NH$_2$, —NHR', —NHR'$_2$, or —(CH$_2$)$_d$OH, wherein each R' is independently a hydrocarbon moiety having from 1 to about 6 carbon atoms, an aryl-containing moiety having from 6 to about 18 carbon atoms, a hydrocarbon moiety having from 1 to about 6 carbon atoms and a terminal carboxylic acid or alcohol, or an aryl-containing moiety having from 6 to about 18 carbon atoms and a terminal carboxylic acid or alcohol.

(iv) r dendrons bonded to the fullerene core and s nondendrons bonded to the fullerene core, wherein:

(iv-a) r is an integer from 1 to 6, inclusive;

(iv-b) s is an integer from 0 to 18, inclusive;

(iv-b) each dendron has at least one protic group which imparts water solubility, (iv-d) each nondendron independently comprises at least one drug, amino acid, peptide, nucleotide, vitamin, or organic moiety, and (iv-e) when r is 1 and the dendron comprises 18 —COOH groups, s is an integer from 1 to 18, inclusive.

* * * * *